United States Patent
Haghighi et al.

(10) Patent No.: US 12,387,324 B2
(45) Date of Patent: Aug. 12, 2025

(54) SYSTEMS, METHODS, AND APPARATUSES FOR IMPLEMENTING DISCRIMINATIVE, RESTORATIVE, AND ADVERSARIAL (DiRA) LEARNING FOR SELF-SUPERVISED MEDICAL IMAGE ANALYSIS

(71) Applicant: Arizona Board of Regents on behalf of Arizona State University, Scottsdale, AZ (US)

(72) Inventors: Fatemeh Haghighi, Tempe, AZ (US); Mohammad Reza Hosseinzadeh Taher, Tempe, AZ (US); Jianming Liang, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 362 days.

(21) Appl. No.: 18/111,136

(22) Filed: Feb. 17, 2023

(65) Prior Publication Data

US 2023/0281805 A1   Sep. 7, 2023

Related U.S. Application Data

(60) Provisional application No. 63/311,846, filed on Feb. 18, 2022.

(51) Int. Cl.
*G06T 7/00* (2017.01)
*G06T 5/00* (2024.01)
(Continued)

(52) U.S. Cl.
CPC .............. *G06T 7/0012* (2013.01); *G06T 5/70* (2024.01); *G06V 10/761* (2022.01);
(Continued)

(58) Field of Classification Search
CPC ..................... G06T 7/0012; G06T 5/70; G06T 2207/20081; G06T 2207/20132;
(Continued)

(56) References Cited

U.S. PATENT DOCUMENTS 8,204,842 B1   6/2012   Zhang et al.
9,811,765 B2   11/2017  Wang et al.
(Continued)

FOREIGN PATENT DOCUMENTS

DE   102016010909 A1   5/2017
EP        3190963 A2   7/2017
(Continued)

OTHER PUBLICATIONS

Tajbakhsh, N. et al., "Computer-aided pulmonary embolism detection using a novel vessel-aligned multi-planar image representation and convolutional neural networks," Medical Image Computing and Computer-Assisted Intervention—MICCAI 2015: 18th International Conference, Munich, Germany, Oct. 5-9, 2015, Proceedings, Part II 18. Springer International Publishing.
(Continued)

*Primary Examiner* — Quang N Vo
(74) *Attorney, Agent, or Firm* — Elliott, Ostrander & Preston, P.C.

(57) ABSTRACT

A Discriminative, Restorative, and Adversarial (DiRA) learning framework for self-supervised medical image analysis is described. For instance, a pre-trained DiRA framework may be applied to diagnosis and detection of new medical images which form no part of the training data. The exemplary DiRA framework includes means for receiving training data having medical images therein and applying discriminative learning, restorative learning, and adversarial learning via the DiRA framework by cropping patches from the medical images; inputting the cropped patches to the
(Continued)

discriminative and restorative learning branches to generate discriminative latent features and synthesized images from each; and applying adversarial learning by executing an adversarial discriminator to perform a min-max function for distinguishing the synthesized restorative image from real medical images. The pre-trained model of the DiRA framework is then provided as output for use in generating predictions of disease within medical images.

20 Claims, 20 Drawing Sheets

(51) Int. Cl.
  *G06T 5/70*  (2024.01)
  *G06V 10/74*  (2022.01)
  *G06V 10/762*  (2022.01)
  *G16H 30/40*  (2018.01)
  *G16H 50/20*  (2018.01)

(52) U.S. Cl.
  CPC ........... *G06V 10/762* (2022.01); *G16H 30/40* (2018.01); *G16H 50/20* (2018.01); *G06T 2207/20081* (2013.01); *G06T 2207/20132* (2013.01); *G06T 2207/30096* (2013.01)

(58) Field of Classification Search
  CPC .......... G06T 2207/30096; G16H 50/20; G16H 30/40; G06V 10/762; G06V 10/761
  See application file for complete search history.

(56) References Cited

U.S. PATENT DOCUMENTS

| | | |
|---|---|---|
| 10,074,038 B2 | 9/2018 | Hsieh et al. |
| 10,460,440 B2 | 10/2019 | Zhang et al. |
| 10,789,691 B2 | 9/2020 | Arai et al. |
| 11,436,725 B2 | 9/2022 | Hosseinzadeh Taher et al. |
| 2018/0196873 A1 | 7/2018 | Yerebakan et al. |
| 2019/0057774 A1 | 2/2019 | Velez et al. |
| 2019/0251694 A1 | 8/2019 | Han et al. |
| 2019/0332900 A1 | 10/2019 | Sjolund et al. |
| 2021/0265043 A1 | 8/2021 | Haghighi et al. |
| 2021/0334994 A1 | 10/2021 | Park et al. |
| 2021/0343014 A1 | 11/2021 | Haghighi et al. |
| 2021/0358123 A1* | 11/2021 | Kearney ................. G16H 30/40 |
| 2022/0036564 A1 | 2/2022 | Ye et al. |
| 2022/0208355 A1* | 6/2022 | Li ........................... G06T 7/174 |
| 2022/0328189 A1 | 10/2022 | Zhou et al. |

FOREIGN PATENT DOCUMENTS

| | | |
|---|---|---|
| EP | 3273387 A1 | 1/2018 |
| EP | 4064124 A1 | 9/2022 |
| WO | 2016040784 A2 | 3/2016 |

OTHER PUBLICATIONS

Tajbakhsh, N. et al., "Convolutional neural networks for medical image analysis: Full training or fine tuning?," IEEE transactions on medical imaging, 35(5), 2016, pp. 1299-1312.

Taleb, A. et al., "3d self-supervised methods for medical imaging," Advances in neural information processing systems, 33, 2020, pp. 18158-18172.

Tao, X. et al., "Revisiting rubik's cube: Self-supervised learning with volume-wise transformation for 3d medical image segmentation," Medical Image Computing and Computer Assisted Intervention—MICCAI 2020: 23rd International Conference, Lima, Peru, Oct. 4-8, 2020, Proceedings, Part IV 23, 2020, Springer International Publishing.

Tian, Y. et al., "What makes for good views for contrastive learning?," Advances in neural information processing systems, 33, 2020, pp. 6827-6839.

Van den Oord, A. et al., "Representation learning with contrastive predictive coding," arXiv:1807.03748v2, 2019.

Vincent, P. et al., "Extracting and composing robust features with denoising autoencoders," Proceedings of the 25th International Conference on Machine Learning, 2008, pp. 1096-1103.

Wang, X. et al., "Chestx-ray8: Hospital-scale chest x-ray database and benchmarks on weakly-supervised classification and localization of common thorax diseases," Proceedings of the IEEE Conference on Computer Vision and Pattern Recognition, 2017, pp. 2097-2106.

Wang, X. et al., "Dense contrastive learning for self-supervised visual pre-training," In Proceedings of the IEEE/CVF Conference on Computer Vision and Pattern Recognition, 2021, pp. 3024-3033.

Wu, Z. et al., "Unsupervised feature learning via non-parametric instance discrimination," In Proceedings of the IEEE Conference on Computer Vision and Pattern Recognition, 2018, pp. 3733-3742.

Xie, E. et al., "Detco: Unsupervised contrastive learning for object detection," Proceedings of the IEEE/CVF International Conference on Computer Vision, 2021, pp. 8392-8401.

Xie, Z. et al., "Propagate yourself: Exploring pixel-level consistency for unsupervised visual representation learning," Proceedings of the IEEE/CVF Conference on Computer Vision and Pattern Recognition, 2021, pp. 16684-16693.

Ye, M. et al., "Unsupervised embedding learning via invariant and spreading instance feature," Proceedings of the IEEE /CVF Conference on Computer Vision and Pattern Recognition, 2019, pp. 6210-6219.

Zbontar, J. et al., "Barlow twins: Self-supervised learning via redundancy reduction," arXiv:2103.03230, 2021.

Zhan, X. et al., Online deep clustering for unsupervised representation learning. In Proceedings of IEEE/CVF Conference on Computer Vision and Pattern Recognition, 2020, pp. 6688-6697.

Zhang, X. et al., "Sar: Scale-aware restoration learning for 3d tumor segmentation," Medical Image Computing and Computer Assisted Intervention—MICCAI 2021: 24th International Conference, Strasbourg, France, Sep. 27-Oct. 1, 2021, Proceedings, Part II 24, 2021, pp. 124-133. Springer International Publishing.

Zhou, H.Y. et al., "Comparing to learn: Surpassing imagenet pretraining on radiographs by comparing image representations," Medical Image Computing and Computer Assisted Intervention—MICCAI 2020: 23rd International Conference, Lima, Peru, Oct. 4-8, 2020, Proceedings, Part I 23, 2020, pp. 398-407. Springer International Publishing.

Zhou, H.Y. et al., "Preservational learning improves self-supervised medical image models by reconstructing diverse contexts," Proceedings of the IEEE/CVF International Conference on Computer Vision, 2021, pp. 3499-3509.

Zhou, Z. et al., "Models genesis," Medical Image Analysis, 67, 2021, p. 101840.

Zhuang, X. et al., "Self-supervised feature learning for 3d medical images by playing a rubik's cube," Medical Image Computing and Computer Assisted Intervention—MICCAI 2019: 22nd International Conference, Shenzhen, China, Oct. 13-17, 2019, Proceedings, Part IV 22. Springer International Publishing.

Armato III, S.G., et al., "The lung image database con—sortium (lidc) and image database resource initiative (idri): a completed reference database of lung nodules on ct scans," Medical physics, 38(2):915-931, 2011.

Azizi, S. et al., "Big self-supervised models advance medical image classification," arXiv:2101.05224, 2021.

Bakas, S. et al., "Identifying the best machine learning algorithms for brain tumor segmentation, progression assessment, and overall survival prediction in the brats challenge," arXiv:1811.02629, 2018.

Bilic, P. et al., "The liver tumor segmentation benchmark (lits)," arXiv:1901.04056, 2019.

Cao, B. et al., "Auto-gan: Self-supervised collaborative learning for medical image synthesis,". Proceedings of the AAAI Conference on Artificial Intelligence, 34(07), 2020, pp. 10486-10493.

(56) References Cited

OTHER PUBLICATIONS

Caron, M. et al., "Deep clustering for unsupervised learning of visual features," In Proceedings of the European Conference on Computer Vision, 2018, pp. 132-149.
Caron, M. et al., "Unsupervised learning of visual features by contrasting cluster assignments," arXiv:2006.09882, 2021.
Chaitanya, K. et al., "Contrastive learning of global and local features for medical image segmentation with limited annotations," In Advances in Neural Information Processing Systems, vol. 33, 2020, pp. 12546-12558.
Chen, H. et al., "Joint generative and contrastive learning for unsupervised person re-identification," Proceedings of the IEEE/CVF Conference on Computer Vision and Pattern Recognition, 2021, pp. 2004-2013.
Chen, L. et al., "Self-supervised learning for medical image analysis using image context restoration," Medical image analysis, 58, 2019, 101539.
Chen, T. et al., "A simple framework for contrastive learning of visual representations," International conference on machine learning, PMLR, 2020, pp. 1597-1607.
Chen, T. et al., "Big self-supervised models are strong semi-supervised learners," Advances in neural information processing systems, vol. 33, 2020, pp. 22243-22255.
Chen, X. et al., "Improved baselines with momentum contrastive learning," arXiv preprint arXiv:2003.04297, 2020.
Chen, X. et al., "Exploring simple siamese representation learning," In Proceedings of the IEEE/CVF Conference on Computer Vision and Pattern Recognition (CVPR), 2021, pp. 15750-15758.
Choe, J. et al., "Evaluating weakly supervised object localization methods right," Proceedings of the IEEE/CVF Conference on Computer Vision and Pattern Recognition, 2020.
Devries, T. et al., "Improved regularization of convolutional neural networks with cutout," arXiv preprint arXiv:1708.04552, 2017.
Doersch, C. et al., "Unsupervised visual representation learning by context prediction," In Proceedings of the IEEE International Conference on Computer Vision, 2015, pp. 1422-1430.
Donahue, J. et al., "Large scale adversarial representation learning," Advances in Neural Information Processing Systems, vol. 32, 2019.
Dumoulin, V. et al., "Adversarially learned inference," In International Conference on Learning Representations, ICLR 2017, Toulon, France, Apr. 24-26, 2017.
Ellis, D.G. et al., "Trialing u-net training modifications for segmenting gliomas using open source deep learning framework," Brainlesion: Glioma, Multiple Sclerosis, Stroke and Traumatic Brain Injuries, 2021, pp. 40-49, Springer International Publishing.
Ermolov, A. et al., "Whitening for self-supervised representation learning," International Conference on Machine Learning, PMLR, 18-24, 2021, pp. 3015-3024.
Esteva, A. et al., "Dermatologist-level classification of skin cancer with deep neural networks," Nature, 542(7639), 2017, pp. 115-118. https://doi.org/10.1038/nature21056.
Feng, R. et al., "Parts2whole: Self-supervised contrastive learning via reconstruction," In Domain Adaptation and Representation Transfer, and Distributed and Collaborative Learning: Second MICCAI Workshop, DART 2020, and First MICCAI Workshop, DCL 2020, Held in Conjunction with MICCAI 2020, Lima, Peru, Oct. 4-8, 2020, Proceedings 2, pp. 85-95. Springer International Publishing.
Feng, R. et al., "Self-supervised Learning: From Parts to Whole," unpublished manuscript.
Gidaris, S. et al., "Unsupervised representation learning by predicting image rotations," arXiv:1803.07728, 2018.
Goodfellow, I. et al., "Generative adversarial nets," Communications of the AMC, 63(11), 2020, pp. 139-144.
Grill, J.B. et al., "Bootstrap your own latent—a new approach to self-supervised learning," Advances in Neural Information Processing Systems, vol. 33, 2020, pp. 21271-21284.
Guo, Z. et al., "Discriminative, restorative, and adversarial learning: Stepwise incremental pretraining," In MICCAI Workshop on Domain Adaptation and Representation Transfer, 2022, pp. 66-76, Cham: Springer Nature Switzerland.
Haghighi, F. et al., "DiRA: Discriminative, restorative, and adversarial learning for self-supervised medical image analysis," In Proceedings of the IEEE/CVF Conference on Computer Vision and Pattern Recognition, 2022, pp. 20824-20834.
Haghighi, F. et al., "Learning semantics-enriched representation via self-discovery, self-classification, and self-restoration," Medical Image Computing and Computer Assisted Intervention—MICCAI 2020: 23rd International Conference, Lima, Peru, Oct. 4-8, 2020, Proceedings, Part I 23, pp. 137-147, Springer International Publishing.
Haghighi, F. et al., "Transferable visual words: Exploiting the semantics of anatomical patterns for self-supervised learning," IEEE Transactions on Medical Imaging, 40(10), 2021, pp. 2857-2868.
He, K. et al., "Deep residual learning for image recognition," Proceedings of the IEEE Conference on Computer Vision and Pattern Recognition, 2016, pp. 770-778.
He, K. et al., "Momentum contrast for unsupervised visual representation learning," Proceedings of the IEEE/CVF Conference on Computer Vision and Pattern Recognition, 2020, pp. 9729-9738.
Hosseinzadeh Taher, M.R. et al., "A systematic benchmarking analysis of transfer learning for medical image analysis," Domain Adaptation and Representation Transfer, and Affordable Healthcare and AI for Resource Diverse Global Health: Third MICCAI Workshop, DART 2021, and First MICCAI Workshop, FAIR 2021, Held in Conjunction with MICCAI 2021, Strasbourg, France, Sep. 27 and Oct. 1, 2021, Proceedings 3. Springer International Publishing.
Irvin, J. et al., "Chexpert: A large chest radiograph dataset with uncertainty labels and expert comparison," arXiv:1901.07031, 2019.
Jaeger, S. et al., "Two public chest x-ray datasets for computer-aided screening of pulmonary diseases," Quantitative imaging in medicine and surgery, 4(6), 2014, p. 475.
Kingma, D.P. et al., "Auto-encoding variational bayes," arXiv:1312.6114, 2014.
Larsson, G. et al., "Colorization as a proxy task for visual understanding," Proceedings of the IEEE conference on computer vision and pattern recognition, 2017, pp. 6874-6883.
Li, J. et al., "Prototypical contrastive learning of unsupervised representations," arXiv:2005.04966, 2021.
Liu, R. et al., "Divco: Diverse conditional image synthesis via contrastive generative adversarial network," In Proceedings of the IEEE/CVF Conference on Computer Vision and Pattern Recognition, 2021, pp. 16377-16386.
Ma, D. et al., "Foundation Ark: Accruing and Reusing Knowledge for Superior and Robust Performance," arXiv:2310.09507v1 [cs.CV], 2023.
McKinney, S.M. et al., "International evaluation of an AI system for breast cancer screening," Nature 577, 202, pp. 89-94. https://doi.org/10.1038/s41586-019-1799-6.
Mustafa, B. et al., "Supervised transfer learning at scale for medical imaging," arXiv:2101.05913, 2021.
Noroozi, M. et al., "Unsupervised learning of visual representations by solving jigsaw puzzles," Computer Vision-ECCV 2016: 14th European Conference, Amsterdam, The Netherlands, Oct. 11-14, 2016, Proceedings, Part VI, 2016, pp. 69-84, Springer International Publishing.
Parmar, G. et al., "Dual contradistinctive generative autoencoder," Proceedings of the IEEE/CVF Conference on Computer Vision and Pattern Recognition, 2021, pp. 823-832.
Pathak, D. et al., "Context encoders: Feature learning by inpainting," Proceedings of the IEEE Conference on Computer Vision and Pattern Recognition, 2016, pp. 2536-2544.
Ronneberger, O. et al., U-net: Convolutional networks for biomedical image segmentation. Medical Image Computing and Computer-Assisted Intervention—MICCAI 2015: 18th International Conference, Munich, Germany, Oct. 5-9, 2015, Proceedings, Part III 18, pp. 234-241, Springer International Publishing.
Selvaraju, R. R. et al., "Grad-cam: Visual explanations from deep networks via gradient-based Localization," Proceedings of the IEEE International Conference on Computer Vision, 2017, pp. 618-626.

(56) References Cited

OTHER PUBLICATIONS

Setio, A.A.A., et al., "Validation, comparison, and combination of algorithms for automatic detection of pulmonary nodules in computed tomography images: the luna16 challenge," Medical image analysis, 42, 2017, pp. 1-13.

Taher, M. R. H. et al., "CAID: Context-aware instance discrimination for self-supervised learning in medical imaging," In International Conference on Medical Imaging with Deep Learning, 2022, pp. 535-551, PMLR.

* cited by examiner

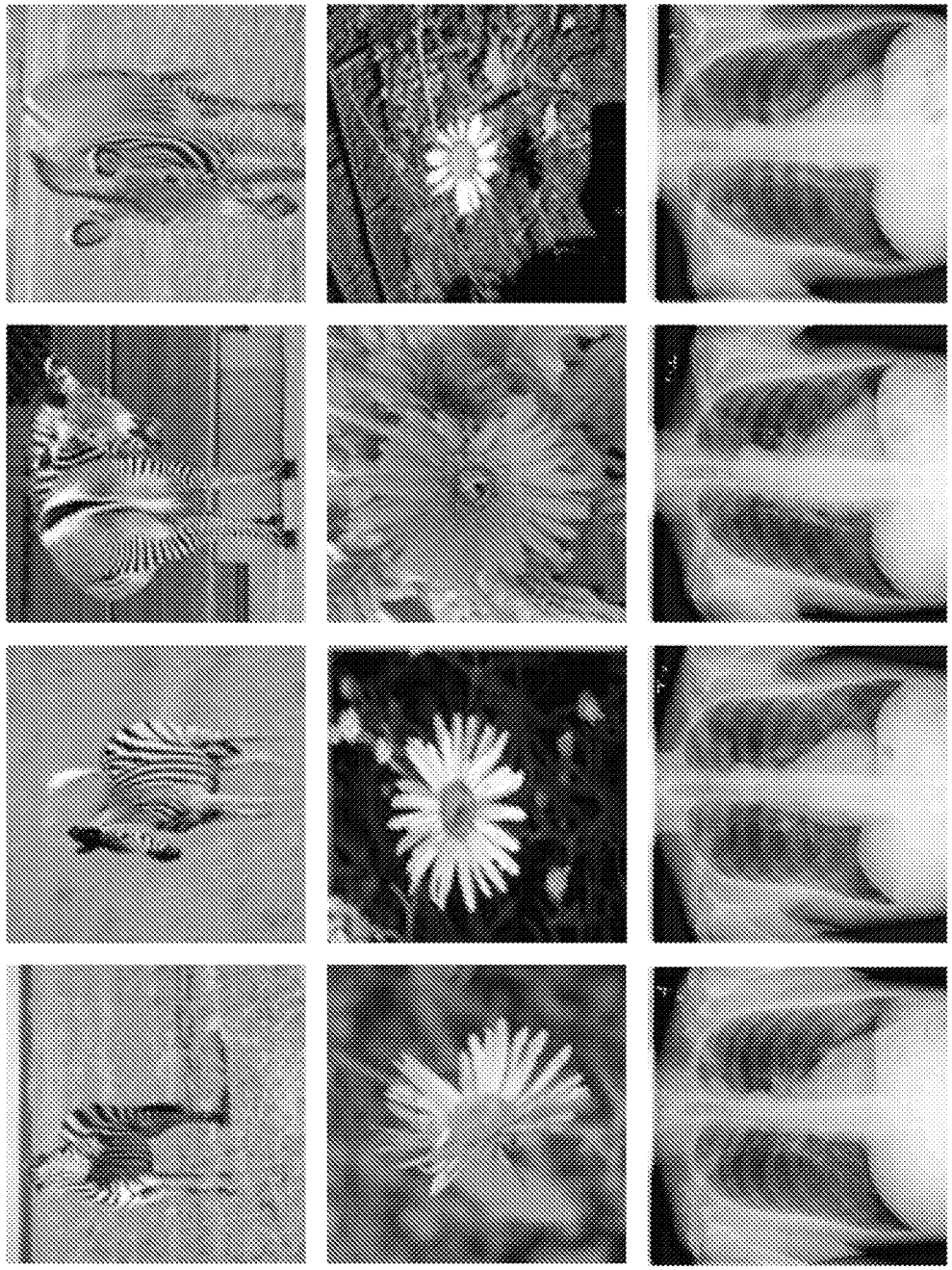

FIG. 2A 201

TABLE 1:

| Method | ChestX-ray14 [AUC (%)] | | | CheXpert [AUC (%)] | | | Montgomery [Dice (%)] | | |
|---|---|---|---|---|---|---|---|---|---|
| | \multicolumn{3}{l|}{Label fraction} | \multicolumn{3}{l|}{Label fraction} | \multicolumn{3}{l|}{Label fraction} |
| | 1% | 25% | 50% | 1% | 25% | 50% | 1% | 25% | 50% |
| MoCo-v2 | 52.99 | 74.89 | 76.71 | 76.87 | 81.70 | 83.23 | 63.69 | 96.44 | 97.60 |
| DiRA$_{MoCo-v2}$ | 59.39 (↑6.4) | 77.55 (↑2.6) | 78.74 (↑2.0) | 78.43 (↑1.5) | 87.12 (↑5.4) | 87.31 (↑4.0) | 72.53 (↑8.8) | 97.06 (↑0.62) | 98.14 (↑0.5) |
| Barlow Twins | 62.43 | 76.23 | 77.59 | 82.85 | 83.74 | 84.66 | 86.79 | 97.49 | 97.68 |
| DiRA$_{Barlow Twins}$ | 62.51 (↑0.08) | 77.18 (↑0.9) | 78.46 (↑0.8) | 83.12 (↑0.2) | 84.20 (↑0.4) | 85.32 (↑0.6) | 87.25 (↑0.4) | 97.62 (↑0.1) | 98.15 (↑0.4) |
| SimSiam | 51.07 | 73.05 | 75.20 | 65.39 | 80.05 | 81.46 | 48.20 | 94.86 | 97.21 |
| DiRA$_{SimSiam}$ | 53.42 (↑2.3) | 74.38 (↑1.3) | 76.43 (↑1.2) | 70.46 (↑5.0) | 81.03 (↑1.0) | 82.70 (↑1.2) | 61.86 (↑13.6) | 96.61 (↑1.7) | 97.91 (↑0.7) |

TABLE 2:

| Method | Pretraining Dataset | Classification [AUC (%)] | | Segmentation [Dice (%)] | |
|---|---|---|---|---|---|
| | | ChestX-ray14 | CheXpert | SIIM-ACR | Montgomery |
| Random | - | 80.31±0.10 | 86.62±0.15 | 67.54±0.60 | 97.55±0.36 |
| Supervised | ImageNet | 81.70±0.15 | 87.17±0.22 | 67.93±1.45 | 98.19±0.13 |
| Supervised | ChestX-ray14 | - | 87.40±0.26 | 68.92±0.98 | 98.16±0.05 |
| DiRA$_{MoCo-v2}$ | ChestX-ray14 | 81.12±0.17 | 87.59±0.28 † ‡ | 69.24±0.41 † * | 98.24±0.09 † ‡ |
| DiRA$_{Barlow\ Twins}$ | ChestX-ray14 | 80.88±0.30 | 87.50±0.27 † * | 69.87±0.68 † ‡ | 98.16±0.06 † * |
| DiRA$_{SimSiam}$ | ChestX-ray14 | 80.44±0.29 | 86.04±0.43 | 68.76±0.69 † * | 98.17±0.11 † * |

FIG. 2C

TABLE 3

| Dataset | Method | | |
|---|---|---|---|
| | Random | TransVW | DiRA$_{TransVW}$ |
| LUNA | 94.25±5.07 | 98.46±0.30 | 98.87±0.61 (↑0.41) |
| LIDC-IDRI | 74.05±1.97 | 77.33±0.52 | 77.51±1.36 (↑0.18) |
| LiTS | 79.76±5.42 | 86.53±1.30 | 86.85±0.81 (↑0.32) |
| BraTS | 59.87±4.04 | 68.82±0.38 | 69.57±1.13 (↑0.75) |
| PE-CAD | 80.36±3.58 | 87.07±2.83 | 86.91±3.27 |

TABLE 4:

| Base | Pretraining dataset | $\mathcal{L}_{dis}$ | $\mathcal{L}_{res}$ | $\mathcal{L}_{adv}$ | Classification [AUC (%)] | | Segmentation [Dice (%)] | |
|---|---|---|---|---|---|---|---|---|
| | | | | | ChestX-ray14 | CheXpert | SIIM-ACR | Montgomery |
| MoCo-v2 | ChestX-ray14 | ✓ | × | × | 80.36±0.26 | 86.42±0.42 | 67.89±1.14 | 98.03±0.22 |
| | | ✓ | ✓ | × | 80.72±0.29 ↑ | 86.86±0.37 ↑ | 68.16±1.07 ↑ | 98.19±0.08 ↑ |
| | | ✓ | ✓ | ✓ | 81.12±0.17 ↑ | 87.59±0.28 ↑ | 69.24±0.41 ↑ | 98.24±0.09 ↑ |
| Barlow Twins | ChestX-ray14 | ✓ | × | × | 80.45±0.29 | 86.90±0.62 | 69.71±0.34 | 98.13±0.13 |
| | | ✓ | ✓ | × | 80.86±0.16 ↑ | 87.44±0.33 ↑ | 69.83±0.29 ↑ | 98.15±0.14 ↑ |
| | | ✓ | ✓ | ✓ | 80.88±0.30 ↑ | 87.50±0.27 ↑ | 69.87±0.68 ↑ | 98.16±0.06 ↑ |
| SimSiam | ChestX-ray14 | ✓ | × | × | 79.62±0.34 | 83.82±0.94 | 67.58±1.89 | 97.72±0.27 |
| | | ✓ | ✓ | × | 79.41±0.42 ↓ | 84.45±0.46 ↑ | 68.35±1.16 ↑ | 98.02±0.21 ↑ |
| | | ✓ | ✓ | ✓ | 80.44±0.29 ↑ | 86.04±0.43 ↑ | 68.76±0.69 ↑ | 98.17±0.11 ↑ |

TABLE 5:

| Method | $\delta = 10\%$ | $\delta = 20\%$ | $\delta = 30\%$ | $\delta = 40\%$ | $\delta = 50\%$ | $\delta = 60\%$ |
|---|---|---|---|---|---|---|
| MoCo-v2 | 54.89 | 39.43 | 24.81 | 14.59 | 7.58 | 2.68 |
| DiRA$_{MoCo-v2}$ | 58.13 (↑3.2) | 42.74 (↑3.3) | 27.52 (↑2.7) | 16.25 (↑1.7) | 9.30 (↑1.7) | 4.35 (↑1.7) |
| Barlow Twins | 50.54 | 38.01 | 26.36 | 16.93 | 9.31 | 4.69 |
| DiRA$_{BarlowTwins}$ | 58.98 (↑8.4) | 45.26 (↑7.2) | 32.71 (↑6.3) | 21.71 (↑4.8) | 13.62 (↑4.3) | 6.26 (↑1.6) |
| SimSiam | 30.24 | 19.80 | 11.46 | 5.62 | 2.30 | 0.79 |
| DiRA$_{SimSiam}$ | 51.07 (↑20.8) | 34.24 (↑14.4) | 20.64 (↑9.2) | 11.32 (↑5.7) | 6.46 (↑4.2) | 2.90 (↑2.1) |

…

SYSTEMS, METHODS, AND APPARATUSES FOR IMPLEMENTING DISCRIMINATIVE, RESTORATIVE, AND ADVERSARIAL (DiRA) LEARNING FOR SELF-SUPERVISED MEDICAL IMAGE ANALYSIS

CLAIM OF PRIORITY

This non-provisional U.S. Utility Patent Application is related to, and claims priority to the U.S. Provisional Patent Application No. 63/311,846, entitled "SYSTEMS, METHODS, AND APPARATUSES FOR IMPLEMENTING DISCRIMINATIVE, RESTORATIVE, AND ADVERSARIAL (DiRA) LEARNING FOR SELF-SUPERVISED MEDICAL IMAGE ANALYSIS," filed Feb. 18, 2022, the entire contents of which are incorporated herein by reference as though set forth in full.

GOVERNMENT RIGHTS AND GOVERNMENT AGENCY SUPPORT NOTICE

This invention was made with government support under R01 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks for the classification and annotation of medical images, and more particularly, to systems, methods, and apparatuses for implementing Discriminative, Restorative, and Adversarial (DiRA) learning for self-supervised medical image analysis, in the context of processing of medical imaging.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

The present state of the art may therefore benefit from the systems, methods, and apparatuses for implementing Discriminative, Restorative, and Adversarial (DiRA) learning for self-supervised medical image analysis, as is described herein.

BRIEF DESCRIPTION OF THE DRAWINGS

Embodiments are illustrated by way of example, and not by way of limitation, and can be more fully understood with reference to the following detailed description when considered in connection with the figures in which:

FIG. 1B depicts various exemplary photographic images and chest X-ray scans, in which the photographic images depict typically large foreground objects with apparent discriminative parts in contrast to medical images which typically contain consistent anatomical structures with semantic information dispersed over the entire images, in accordance with described embodiments;

FIG. 2A depicts Table 1 which details transfer learning under different downstream label fractions, in accordance with described embodiments;

FIG. 2C depicts Table 3 which depicts a comparison with a restorative self-supervised method, in accordance with described embodiments;

DETAILED DESCRIPTION

Described herein are systems, methods, and apparatuses for implementing Discriminative, Restorative, and Adversarial (DiRA) learning for self-supervised medical image analysis.

Discriminative learning, restorative learning, and adversarial learning have proven beneficial for self-supervised learning schemes in computer vision and medical imaging. Existing efforts, however, omit their synergistic effects on each other in a ternary setup, which, as demonstrated herein by experimental results, can significantly benefit deep semantic representation learning. To realize this vision, the DiRA framework and platform as described herein was developed as the first framework that unites discriminative, restorative, and adversarial learning in a unified manner to collaboratively glean complementary visual information from unlabeled medical images for fine-grained semantic representation learning.

The extensive experiments which are summarized below demonstrate that disclosed DiRA methodology (1) encourages collaborative learning among three learning ingredients, resulting in more generalizable representation across organs, diseases, and modalities; (2) outperforms fully supervised ImageNet models and increases robustness in small data regimes, reducing annotation cost across multiple medical imaging applications; (3) learns fine-grained semantic representation, facilitating accurate lesion localization with only image-level annotation; and (4) enhances state-of-the-art restorative approaches, revealing that DiRA is a general mechanism for united representation learning.

Figure 1A:
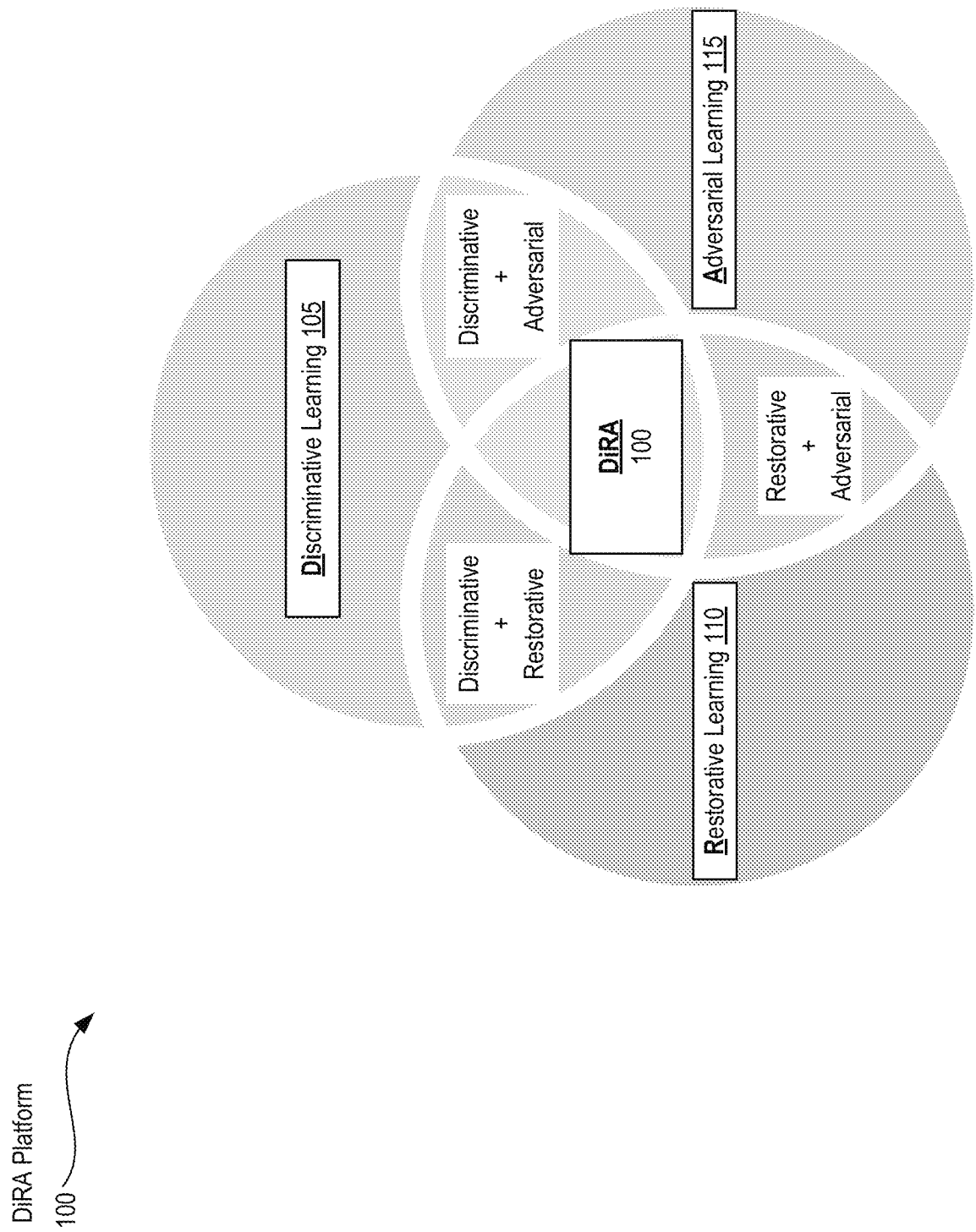
FIG. 1A depicts a novel SSL framework which unites discriminative, restorative, and adversarial learning in a unified manner, identified herein as the DiRA framework, in accordance with disclosed embodiments.

FIG. 1A depicts a novel SSL framework which unites discriminative, restorative, and adversarial learning in a unified manner, identified herein as the DiRA framework, in accordance with disclosed embodiments.

In the field of medical image analysis, Self-supervised learning (SSL) aims to learn generalizable representations without using any expert annotation. The representation learning approaches in the SSL paradigm can be categorized into three main groups: (1) discriminative learning, which utilizes encoders to cluster instances of the same (pseudo) class and distinguish instances from different (pseudo) classes; (2) restorative learning, which utilizes generative models to reconstruct original images from their distorted versions; and (3) adversarial learning, which utilizes adversary models to enhance restorative learning. In computer vision, discriminative SSL approaches, especially contrastive learning currently offer state-of-the-art (SOTA) performance, surpassing standard supervised ImageNet models in some tasks. In medical imaging, however, restorative SSL methods compared to discriminative approaches presently reach a new height in performance.

Despite the critical contributions of discriminative, restorative, and adversarial learning to SSL performance, there is no presently known SSL method which simultaneously employs all three learning ingredients. The novel DiRA platform 100 as described herein implements a novel SSL framework which unites discriminative learning 105, restorative learning 110, and adversarial learning 115 in a unified manner to collaboratively glean complementary visual information from unlabeled data for fine-grained semantic representation learning, resulting in the DiRA platform 100, as shown.

One may inquire, therefore, "precisely what contributes to the popularity differences between discriminative and restorative methods in computer vision and in medical imaging?" Furthermore, from an extensive literature review, it was discovered that no presently known SSL method exploits all three learning components simultaneously. Therefore, one may further inquire: "Can discriminative, restorative, and adversarial learning be seamlessly integrated into a single framework to foster collaborative learning for deep semantic representation, yielding more powerful models for a broad range of applications?"

FIG. 1B depicts various exemplary photographic images and chest X-ray scans, in which the photographic images depict typically large foreground objects with apparent discriminative parts in contrast to medical images which typically contain consistent anatomical structures with semantic information dispersed over the entire images, in accordance with described embodiments. For example, the example images of zebras 181 and the example images of daisies 182 all depict expected large foreground objects with apparent discriminative parts.

Unlike the depicted exemplary photographic images 101, medical images, such as the example medical images showing chest anatomy 183, contain consistent anatomical structures with semantic information dispersed over the entire images. As a result, recognition tasks in photographic images are mainly based on high-level features, while medical tasks demand holistic fine-grained discriminative features captured throughout images.

In seeking answers to the two questions presented above, the following insights were gained: Computer vision and medical imaging tasks embrace the spirit of evil in opposite ways, originating from the marked differences between photographic and medical images. For instance, photographic images (e.g., 181 and 182), particularly those in ImageNet, have large foreground objects with apparent discriminative parts, residing within the varying backgrounds.

Thus, object recognition tasks in photographic images are primarily based on high-level features captured from discriminative regions. In contrast, medical images generated from a particular imaging protocol exhibit consistent anatomical structures (e.g., such as the chest anatomy medical images at element 183), with clinically relevant information dispersed over the entire image.

In particular, high-level structural information, such as the anatomical structures and their relative spatial orientations, are essential for the identification of normal anatomy and various disorders. Importantly, medical tasks require much stronger attention to fine-grained details within images as identifying diseases, delineating organs, and isolating lesions rely on subtle, local variations in texture. Therefore, recognition tasks in medical images benefit from complementary high-level and fine-grained discriminative features captured throughout images.

According to systematical analysis of the experimental results discussed below, the following understandings were gained: (1) discriminative learning excels in capturing high-level (global) discriminative features, (2) restorative learning is good at conserving fine-grained details embedded in local image regions, and (3) adversarial learning consolidates restoration by conserving more fine-grained details.

Putting these understandings and fundamental differences between photographic and medical images together would explain why restorative learning is preferred in medical imaging while discriminative learning is preferred in computer vision. More importantly, these new and intriguing insights were captured into the integrated trio of discriminative learning 105, restorative learning 110, and adversarial learning 115 as represented by the depicted DiRA platform (refer again to element 100 at FIG. 1A), providing the effective features required for medical recognition tasks— not only high-level anatomical representations but also fine-grained discriminative cues embedded in the local parts of medical images.

Figure 1C:
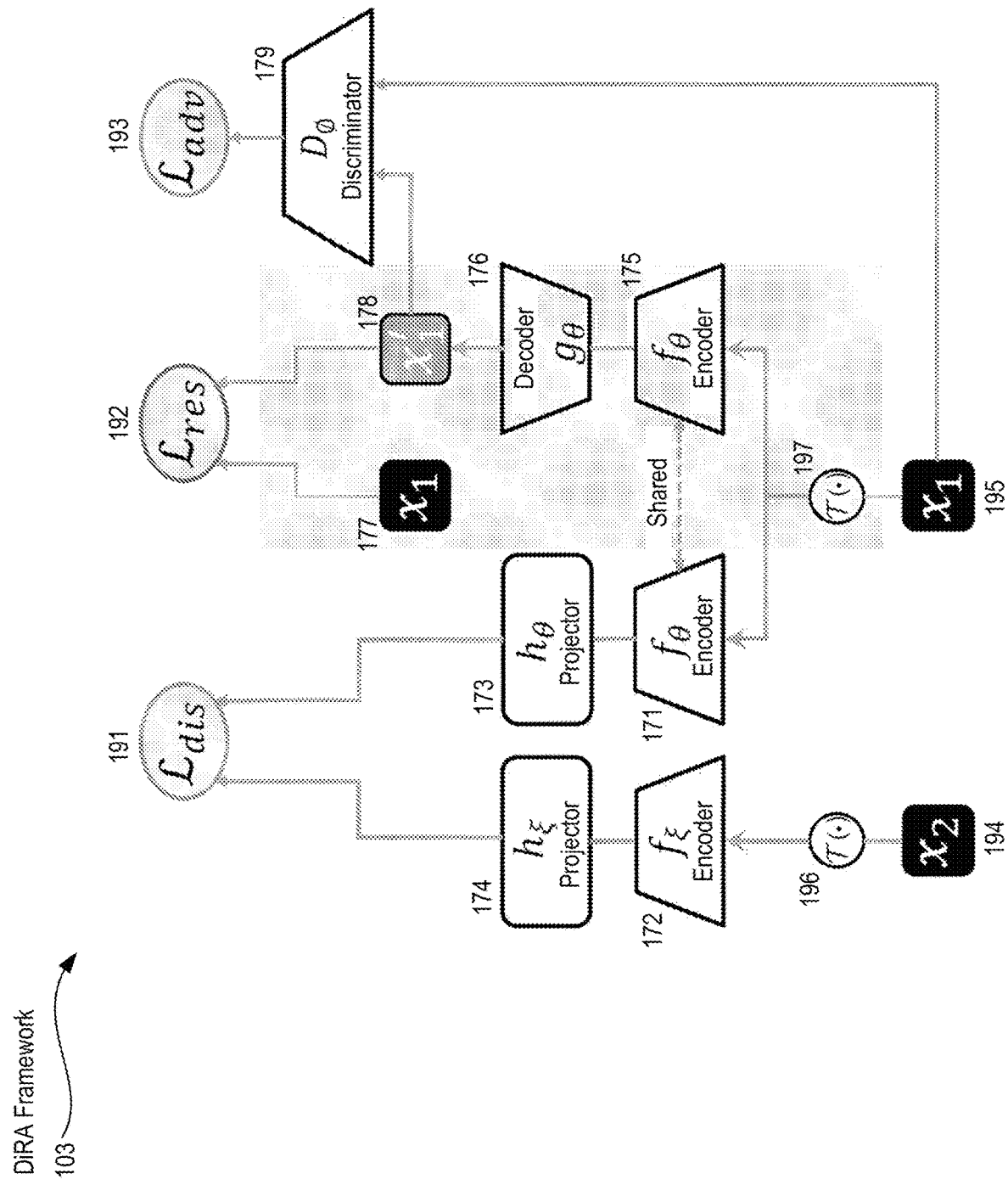
FIG. 1C depicts the novel DiRA framework in greater detail, in accordance with disclosed embodiments.

FIG. 1C depicts the novel DiRA framework 103 in greater detail, in accordance with disclosed embodiments.

As shown here, the DiRA framework consists of three learning ingredients, namely discriminative learning 191, restorative learning 192, and adversarial learning 193. Given two input patches $x_1$ and $x_2$ (elements 194 and 195 respectively), the input patches are then perturbed with T(•) at element 196 and 197, and then each is given as input to the discrimination 191 and restoration 192 branches. The discrimination branch at element 191 consists of encoders $f_\theta$ and $f_\varepsilon$ (elements 171 and 172 respectively), and projectors $h_\theta$ and $h_\varepsilon$ (elements 173 and 174 respectively) and maximizes the agreement between (high-level) embedding vectors of samples from the same (pseudo) class. The restoration branch at element 192 consists of encoder $f_\theta$ at element 175 and decoder $g_\theta$ at element 176, and maximizes the (pixel-level) agreement between original sample $x_1$ at element 177 and restored $x'_1$ at element 178, as depicted. Adversarial discriminator $D_\phi$ at element 179, contrasts the original samples with the restored ones, reinforcing the restoration to preserve more fine-grained details.

With reference again to the novel DiRA framework 103 as depicted at FIG. 1C, a systematical analysis of the described methodology has yielded the following understandings: (1) discriminative learning excels in capturing high-level (global) discriminative features, (2) restorative learning is good at conserving fine-grained details embedded in local image regions, and (3) adversarial learning consolidates restoration by conserving more fine-grained details.

Based on the insights above, the novel self-supervised learning framework described herein, called DiRA, provides improvement over prior techniques by uniting discriminative learning, restorative learning, and adversarial learning in a unified manner to glean complementary visual information from unlabeled medical images.

The extensive experiments, for which the results of which are documented by Tables 1 through 5 as set forth at FIGS. 2A through 2E (discussed in greater detail below), demonstrate that (1) DiRA encourages collaborative learning among three learning components, resulting in more generalizable representation across organs, diseases, and modalities (refer to FIG. 4 which is discussed in greater detail below); further, (2) DiRA outperforms fully supervised ImageNet models and increases robustness in small data regimes, thereby reducing annotation cost in medical imaging (refer to Table 1 and Table 2); still further, (3) DiRA learns fine-grained representations, facilitating more accurate lesion localization with only image-level annotations (refer to FIG. 5 which is discussed in greater detail below); and finally, (4) DiRA enhances SOTA restorative approaches, showing that DiRA is a general framework for united representation learning (refer to Table 3).

Thus, the novel self-supervised learning framework described herein, called DiRA, provides at least the following contributions: (1) insights have been gained into the synergy of discriminative, restorative, and adversarial learning in a ternary setup, realizing a new paradigm of collaborative learning for SSL; (2) the first self-supervised learning framework that seamlessly unites discriminative, restorative, and adversarial learning in a unified manner, setting a new SOTA for SSL in medical imaging is provided in a usable and experimentally verified manner; and (3) a thorough and insightful set of experimental results demonstrate not only DiRA's generalizability but also its potential to take a fundamental step towards developing universal representations for medical imaging.

Discriminative self-supervised learning: Discriminative methods may be divided into class-level and instance-level discrimination. Class-level discrimination methods group images based on certain criteria, assign a pseudo label to each group, and train a model to discriminate the images based on their pseudo labels, such as rotation degrees and cluster assignments. Conversely, instance-level discrimination methods treat each image as a distinct class, and maximize the similarity of representations derived from different views of the same image, seeking to learn transformation invariant representations. Instance-level discriminative learning has been investigated in various forms, including contrastive learning, asymmetric networks, and redundancy reductions.

However, both class-level and instance-level approaches in discriminative learning have shown failures in tasks that require finer-grained features. With reference to FIG. 1C, the DiRA framework 103 described herein addresses this limitation by incorporating restorative and adversarial learning, which not only improves discriminative learning but also yields fine-grained representations required for medical imaging tasks.

Restorative and adversarial self-supervised learning: The key objective for a restorative method is to faithfully reconstruct the distribution of data. In the SSL context, multiple pretext tasks are formulated to reconstruct the perturbed images using generative models. The advance of GANs has led to a new line of research in unsupervised learning, using adversarial learning to generate transferable representations. While recent works have demonstrated impressive results by employing large-scale generative models, it remains unclear to what extent generative models can encapsulate high-level structures.

With reference again to FIG. 1C, the DiRA framework 103 alleviates this limitation by bringing the advantages of discriminative learning into generative models. Through discriminating image samples, generative models are encouraged to capture global discriminative representations rather than superficial representations, leading to a more pronounced embedding space.

Self-supervised learning in medical imaging: Due to the lack of large-scale annotated datasets, SSL created substantial interest in medical imaging. Motivated by the success in computer vision, recent discriminative methods concentrate on instance-level discrimination. For example, a comprehensive benchmarking study evaluated the efficacy of existing instance discrimination methods pre-trained on ImageNet for diverse medical tasks, whereas others working in the technical space adjusted contrastive-based methods on medical images. Prior known methodologies in this space have focused on restorative approaches, including the most recent study which proposed TransVW specifically and which showed promising advancements by combining discriminative and restorative components into a single SSL framework.

Notably, however, the DiRA framework 103 as depicted at FIG. 1C distinguishes itself from all previously known works by demonstrating at least two key advances: Firstly, (1) by employing discriminative, restorative, and adversarial learning simultaneously in a unified framework; and secondly, (2) by providing a general representation learning framework that is compatible with existing discriminative and restorative methods, regardless of their objective functions.

The DiRA framework: As is depicted at FIG. 1C, the DiRA framework 103 is an SSL framework comprised of three key components: (1) Discrimination (referred to as Di) that aims to learn high-level discriminative representations, (2) Restoration (referred to as R) that aims to enforce the model to conserve fine-grained information about the image by focusing on more localized visual patterns, and (3) Adversary (referred to as A) that aims to further improve feature learning through the restoration component.

By integrating these components into a unified framework, the DiRA framework 103 captures comprehensive information from images, providing more powerful representations for various downstream tasks. In the discussion that follows, each component is first introduced by abstracting a common paradigm and then by describing the joint training loss.

Discriminative learning: Discriminative learning can be thought of as training an encoder to maximize agreement between instances of the same (pseudo) class in the latent space via a discriminative loss.

As illustrated in FIG. 1C, the discriminator branch at element 191 is comprised of two twin backbone networks $f_\theta$ and $f_\varepsilon$ (elements 171 and 172) and projection heads $h_\theta$ and $h_\varepsilon$ (elements 173 and 174). As utilized herein, $f_\theta$ at element 171 is a regular encoder, while $f_\varepsilon$ at element 172 can be a momentum encoder or share weights with the other encoder identified as $f_\theta$ at element 175.

Given two patches $x_1$ and $x_2$ at elements 194 and 195, which are cropped from the same image or different images, an augmentation function $T(\cdot)$ at elements 196 and 197) is first applied on them. The two augmented patches are then processed by $f_\theta$ and $f_\varepsilon$ (elements 171 and 172) networks to generate latent features $y_1 = f_{74}(T(x_1))$ and $y_2 = f_\varepsilon(T(x_2))$. The projection heads $h_\theta$ and $h_\varepsilon$ (elements 173 and 174) projects the latent features to a unit sphere and output projections $z_1 = h_\theta(y_1)$ and $z_2 = h_{249}(y_2)$.

The discriminator's objective is to maximize the similarity between the embedding vectors obtained from two samples of the same (pseudo) class, set forth below as equation (1): $L_{dis} = l(z_1, z_2)$, where $l(z_1, z_2)$ is the similarity/distance function that measures compatibility between $z_1$ and $z_2$.

According to the described embodiments, the DiRA platform is a general framework that allows various choices of discrimination tasks without any constraint. As such, the declaration of class might range from considering every single image as a class (instance discrimination) to clustering images based on a similarity metric (cluster discrimination).

Accordingly, patches $x_1$ and $x_2$ at elements 194 and 195 can be two views of the same image or two samples from the same cluster. Based on the nature of the discrimination task, the instantiation of $L_{dis}$ can utilize cross-entropy, contrastive, redundancy reduction techniques, etc., that allow various choices of discrimination tasks without any constraint.

Restorative learning: The restorative learning branch at element 192 aims to enhance discrimination learning by leveraging fine-grained visual information. As shown in FIG. 1C, the restoration branch 192 is comprised of an encoder $f_\theta$ at element 175, and decoder $g_\theta$ at element 176, where encoder $f_\theta$ at element 175 is shared with the discrimination branch 191. Given the input sample $x_1$ at element 195 distorted by T at element 197, the encoder $f_\theta$ and decoder $g_\theta$ (elements 175 and 176) aim to map the distorted sample back to the original one, for instance, $f_\theta, g_\theta : (x,T) \mapsto x$. The networks $f_\theta$ and $g_\theta$ at elements 175 and 176 are trained by minimizing the distance between the original sample and the restored one at pixel-level, according to equation (2), as follows:

$$\mathcal{L}_{res} = \mathbb{E}_x \operatorname{dist}(x_1, x'_1)$$

where $x'_1 = g_\theta(f_\theta(T(x_1)))$ denotes the restored image and where $\operatorname{dist}(x_1, x'_1)$ presents the distance function that measures similarity between $x_1$ and $x'_1$ (at elements 177 and 178) such as $L_1$ or $L_2$.

Adversarial learning: Adversarial learning (element 193) aims to reinforce $f_\theta$ (shared networks depicted by elements 171 and 175) by measuring how realistic the restored images are. As such, adversarial discriminator $D_\phi$ at element 179 is formulated to discriminate (distinguish) the set of training images from the set of synthesized images, guiding encoder $f_\theta$ (element 175) to capture more informative features from images so that $g_\theta$ at element 176 can reproduce the original images effectively. Therefore, the encoder $f_\theta$ (elements 175) and decoder $g_\theta$ at element 176 play a min-max game with adversarial discriminator $D_\phi$ at element 179, and are optimized jointly with an adversarial loss according to equation (3), as follows:

$$\mathcal{L}_{adv} = \mathbb{E}_x[\log D_\phi(x_1)] + \mathbb{E}_x[\log(1 - D_\phi(x'_1))].$$

Joint training: Finally, the combined objective for the proposed DiRA framework, according to equation (4), becomes:

$$\mathcal{L} = \lambda_{dis} * \mathcal{L}_{dis} + \lambda_{res} * \mathcal{L}_{res} + \lambda_{adv} * \mathcal{L}_{adv},$$

where $\lambda_{dis}$, $\lambda_{res}$, and $\lambda_{adv}$ are multiplication factors that determine the relative importance of different losses. Through the described unified training scheme, the DiRA framework (element 103 at FIG. 1C) thus learns a representation that preserves fine-grained details of the samples while being discriminative among the image classes. In particular, the formulation of $L_{dis}$ operates to encourage the model to capture high-level discriminative features. Moreover $L_{res}$ operates to enforce the model to encode fine-grained information from the images by focusing on pixel-level visual patterns. This results in more descriptive feature embeddings that elevate the discrimination task. Finally, $L_{adv}$ operates to elevate restoration-based learning through capturing more informative features.

Implementations Details

Pre-training protocol: The described DiRA framework (element 103 at FIG. 1C) is a general framework that is compatible with existing self-supervised discriminative and restorative methods, regardless of their objective functions. To assess the effectiveness of the described framework, recent state-of-the-art 2D and 3D self-supervised methods are adopted into the DiRA framework, as described below. The pretrained models with DiRA are identified as DiRA subscripted by the original method name.

2D image pretraining settings: The DiRA framework was applied to MoCo-v2, Barlow Twins, and SimSiam for 2D image self-supervised learning. All the DiRA models were pretrained from scratch on the training set of the ChestX-ray 14 dataset.

For each of these three discrimination tasks, the experiments follow the original methods in the formulation of $L_{dis}$, projection head architecture and hyperparameters settings.

Furthermore, the experiments optimize the encoder and decoder networks $f_\theta$ and $g_\theta$, following the optimization setups (optimizer, learning rate and decay). For all methods, the experiments employ a 2D U-Net with a standard ResNet-50 backbone as the $f_\theta$ and $g_\theta$. The experiments adopt the commonly used mean square error (MSE) as the $L_{res}$. The adversarial discriminator network $D_\phi$ consists of four convolutional layers with the kernel size of 3×3, and is trained using the Adam optimizer with a learning rate of 2e-4 and $(\beta_1, \beta_2)=(0.5, 0.999)$. Each of $L_{dis}$, $L_{res}$, and $L_{adv}$ are empirically set to 10, 0.001, and 1, respectively. Input images are first randomly cropped and resized to 224×224; the image augmentation function T(•) includes random horizontal flipping, color jittering, and Gaussian blurring. Additionally, the experiments apply cutout and shuffling to make the restoration task more challenging.

3D volume pretraining settings: Further experiments apply the DiRA framework described herein to TransVW, a state-of-the-art 3D self-supervised learning for medical imaging. Such experiments adapt TransVW in the DiRA framework by adding an adversarial discriminator $D_\phi$ into its training scheme. For the sake of fair comparisons, the experiments utilize the publicly available code of Trans VW for the settings of instance discrimination and restoration tasks. Moreover, similar to publicly released TransVW, the DiRA models are pre-trained from scratch using 623 chest CT scans in LUNA dataset. The experiments use 3D U-Net as the encoder-decoder network and a classification head including fully-connected layers. The adversarial discriminator Do includes four convolutional blocks with the kernel size 3×3×3. Each of $L_{res}$, $L_{adv}$, and $L_{dis}$ are empirically set to 100, 1, and 1, respectively. Each of $f_{74}$, $g_\theta$, and $D_\phi$ were optimized for 200 epochs using Adam with a learning rate of 1e-3 and batch size of eight (8).

Transfer Learning Protocol

Target tasks and datasets: The inventors evaluated the effectiveness of the DiRA framework's representations in transfer learning to a diverse suite of nine (9) common but challenging 2D and 3D medical imaging tasks, including: ChestX-ray14, CheXPert, SIIM-ACR, and NIH Montgomery for each of 2D models. For the 3D models, LUNA, PE-CAD, LIDC-IDRI, LiTS, and BraTS are utilized (refer to the discussion below in the context of FIGS. 5A, 5B, and 5C and also Table 5, as set forth at FIG. 2E, element 205, for details of each dataset).

These tasks encompass various label structures (multi-label classification and pixel-level segmentation), diseases (brain tumors and thoracic diseases, such as lung nodules, pulmonary emboli, and pneumothorax), organs (lung, liver, brain), and modalities (X-ray, CT, MRI). Moreover, these tasks contain many hallmark challenges encountered when working with medical images, such as imbalanced classes, limited data, and small-scanning areas for the pathology of interest. The official data split of these datasets was utilized when available; otherwise, the data was randomly divided into 80% and 20% portions for training and testing, respectively.

Fine-tuning settings: The experiments transfer the pre-trained (1) encoder $f_\theta$ of the DiRA platform to the classification tasks, and (2) encoder and decoder of the DiRA framework ($f_\theta$ and $g_\theta$) to segmentation tasks. Generalization of DiRA representations were evaluated by fine-tuning all the parameters of downstream models. The AUC (area under the ROC curve), and the IoU (Intersection over Union) and Dice coefficient were utilized for evaluating classification and segmentation performances, respectively.

Each downstream task was optimized with the best performing hyperparameters (refer to the discussion below in the context of FIGS. 5A, 5B, and 5C and also Table 5, as set forth at FIG. 2E, element 205, for details of each dataset). An early-stop mechanism was utilized using 10% of the training data as the validation set to avoid over-fitting. Each method was run ten times on each downstream task the average, standard deviation, and statistical analysis was reported based on an independent two-sample t-test.

Figure 3A:
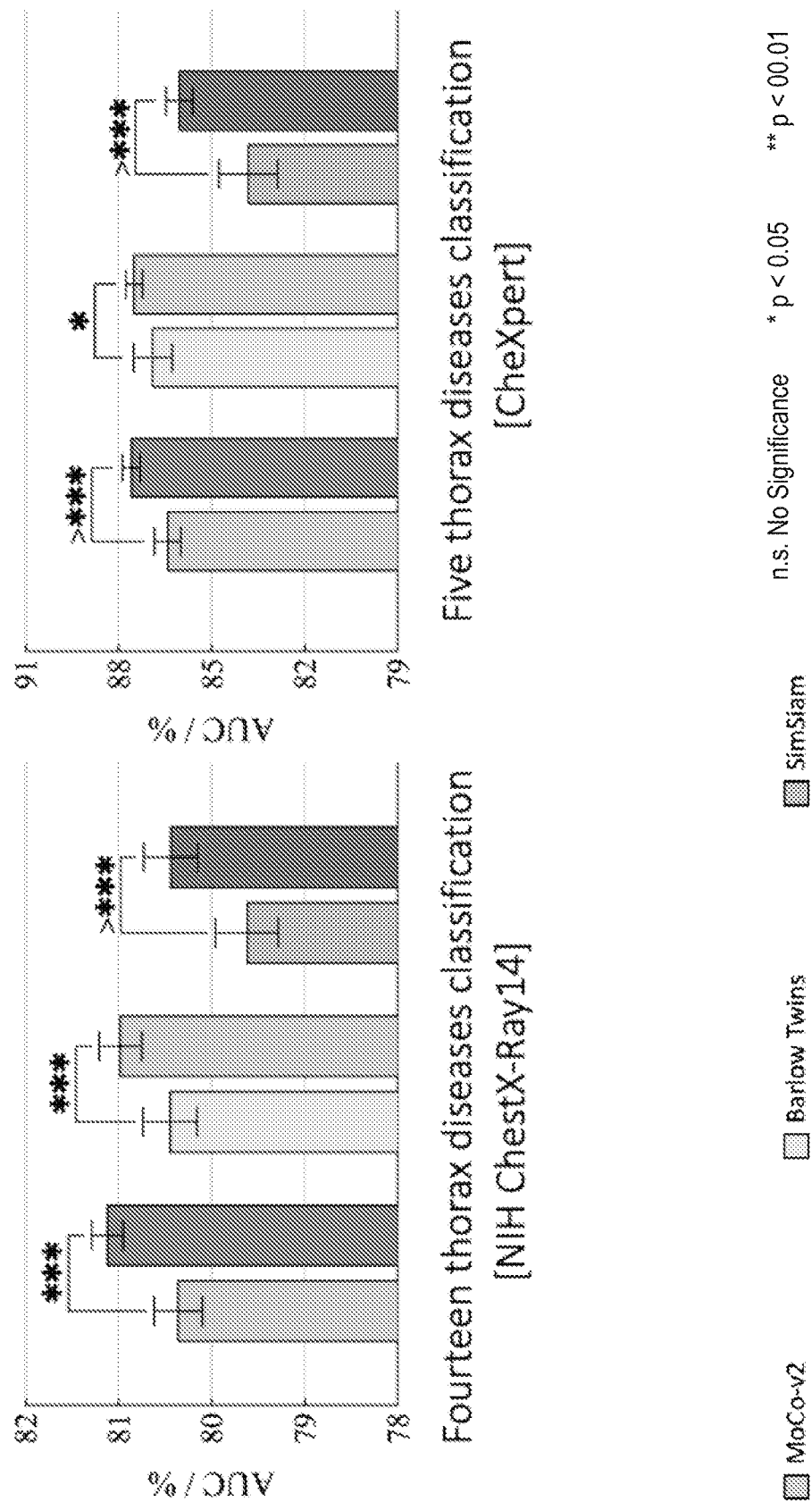
FIGS. 3A and 3B present a comparison with discriminative self-supervised methods, in accordance with described embodiments.
Figure 3B:
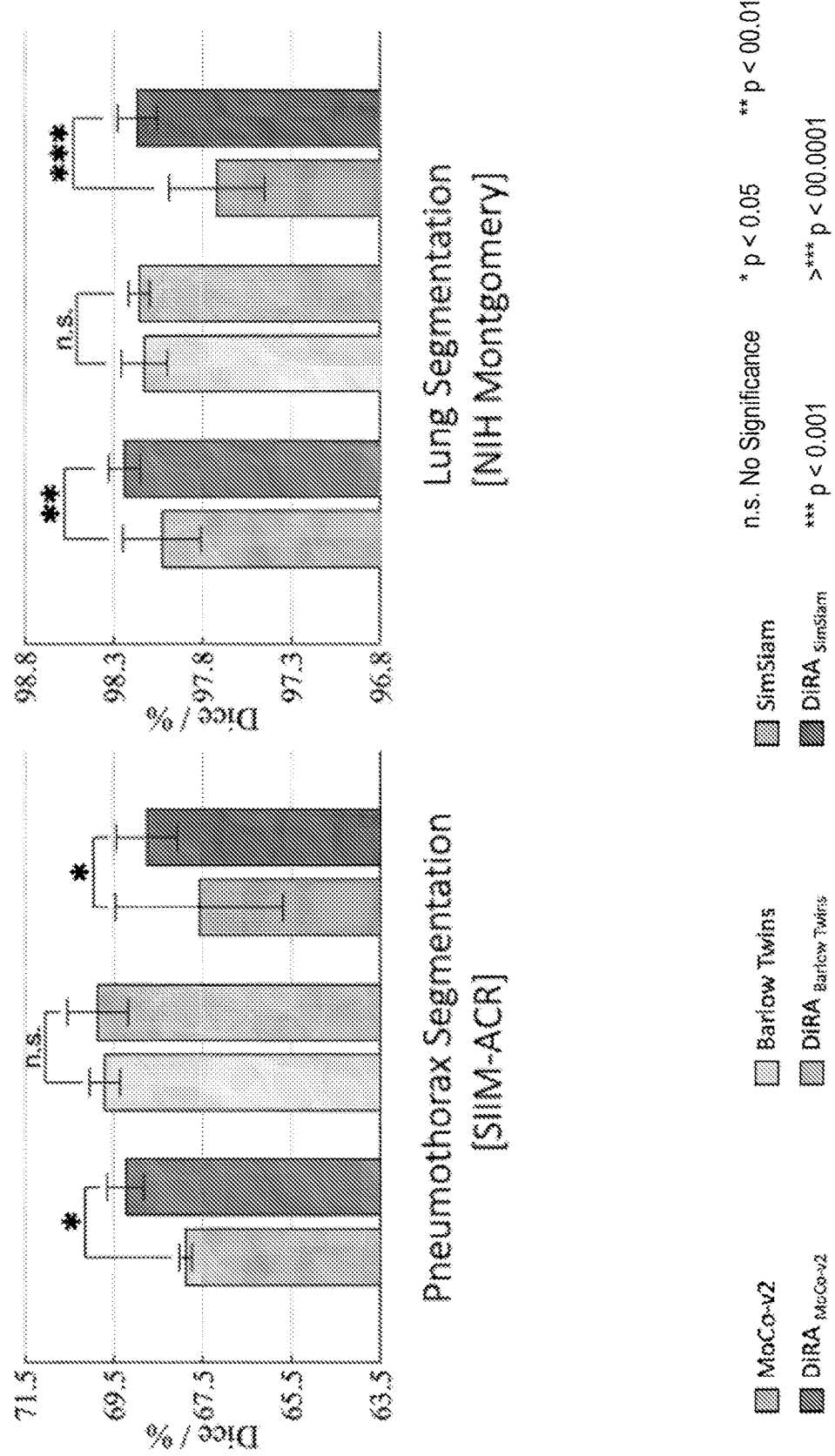

FIGS. 3A and 3B present a comparison with discriminative self-supervised methods, in accordance with described embodiments. Specifically, the novel DiRA framework is applied to three representative state-of-the-art self-supervised methods with different discrimination objectives. For each of MoCo-v2, Barlow Twins, and SimSiam, the DiRA framework empowers discriminative methods to capture more fine-grained representations, yielding significant ($p<0.05$) performance improvements on four downstream tasks, as shown.

Results: A comprehensive set of experiments were conducted to better understand not only the properties of the proposed self-supervised learning framework but also its generalizability across a wide range of nine (9) downstream tasks. Through the following groups of experiments, it was established that DiRA (1) enriches existing discriminative approaches, capturing a more diverse visual representation that generalizes better to different tasks; (2) addresses the annotation scarcity challenge in medical imaging, providing an annotation-efficient solution for medical imaging; (3) learns fine-grained features, facilitating more accurate lesion localization with only image-level annotation; and (4) improves SOTA restorative approaches, demonstrating that DiRA is a general framework for united representation learning.

DiRA Framework Enriches Discriminative Learning

Experimental setup: To study the flexibility and efficacy of the proposed self-supervised framework, the experiments applied DiRA to three recent state-of-the-art self-supervised methods with diverse discrimination objectives: MoCo-v2, Barlow Twins, and SimSiam. To evaluate the quality of the learned representations and ascertain the generality of our findings, a broader range of four target tasks were considered, covering classification (ChestX-Ray14 and CheXpert) and segmentation (SIIM-ACR and Montgomery).

Results: As depicted at FIGS. 3A and 3B, utilizing the self-supervised DiRA framework consistently enhances its underlying discriminative method across all tasks (i) ChestX-ray14, (ii) CheXpert, (iii) SIIM-ACR, and (iv) NIH Montgomery. Compared to the original methods, $DiRA_{MoCo-v2}$ showed increased performance by 0.76%, 1.17%, 1.35%, and 0.21%, respectively. Similarly, $DiRA_{Barlow\ Twins}$ showed increased performance by 0.43%, 0.60%, 0.16%, and 0.03%. Finally, $DiRA_{SimSiam}$ showed increased performance by 0.82%, 2.22%, 1.18%, and 0.45%. These results imply that DiRA is a comprehensive representation learning framework that encourages existing self-supervised instance discriminative approaches to retain more fine-grained information from images, enriching their visual representation and allowing them to generalize to different medical tasks more effectively.

DiRA Improves Robustness to Small Data Regimes

Experimental setup: Further investigated through experimentation was the robustness of representations learned with DiRA in small data regimes to determine if the learned representation can serve as a proper foundation for fine-tuning. Random selections of 1%, 25%, and 50% of training data were taken from ChestX-ray14, CheXpert, and Montgomery, and then the experimental setup fine-tuned the self-supervised pre-trained models on these training data subsets.

FIG. 2A depicts Table 1 (element 201) which details transfer learning under different downstream label fractions, in accordance with described embodiments.

As shown here, DiRA models combat overfitting in low data regimes and provide stronger representations for downstream tasks with limited annotated data. For each downstream task, the average performance is reported over multiple runs. The upward arrow symbol (↑) shows the improvement of DiRA models compared with the underlying discriminative method.

Results: As is set forth at Table 1 (refer to element 201 of FIG. 2A), the DiRA pre-trained models outperform their counterparts' original methods in all subsets, 1%, 25%, and 50%, across ChestX-ray14, CheXpert, and Montgomery. In particular, the average of improvement for MoCo-v2 and SimSiam across all three downstream tasks in each underlying subset garnering: (1) 5.6% and 7% when using 1%, (2) 2.9% and 1.3% when using 25%, and (3) 2.2% and 1% when using 50%. As seen in 1%, DiRA outperforms its counterparts MoCo-v2 and SimSiam by a large margin, demonstrating the potential of the DiRA framework for combating overfitting in extreme low data regimes. Although the Barlow Twins is more resistant to low data regimes than the previous two approaches, the DiRA framework still improves its performance by 0.5%, 0.5%, and 0.6% on average across all three datasets when using 1%, 25%, and 50% of labeled data, respectively. In summary, the experimental results in the low-data regimes demonstrate the DiRA framework's superiority for providing more robust and transferable representations that can be harnessed for downstream tasks with limited amounts of data, thereby reducing annotation costs.

Figure 4A:
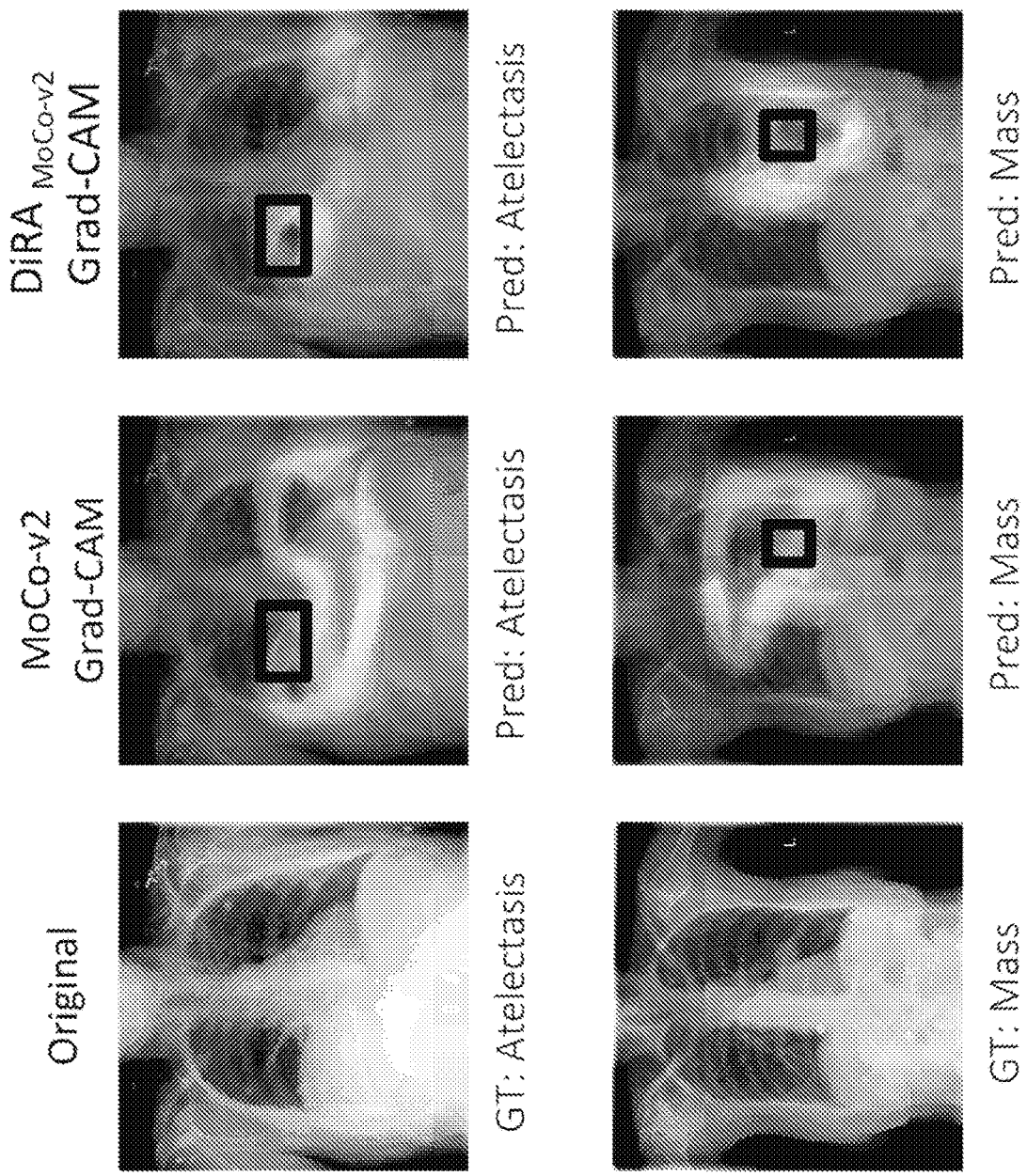
FIGS. 4A, 4B, and 4C provide visualizations of Grad-CAM heatmaps for (a) MoCo-v2 vs. $DiRA_{MoCo\text{-}v2}$, (b) Barlow Twins vs. $DiRA_{BarlowTwins}$, and (c) SimSiam vs. $DiRA_{SimSiam}$, in accordance with described embodiments.
Figure 4B:
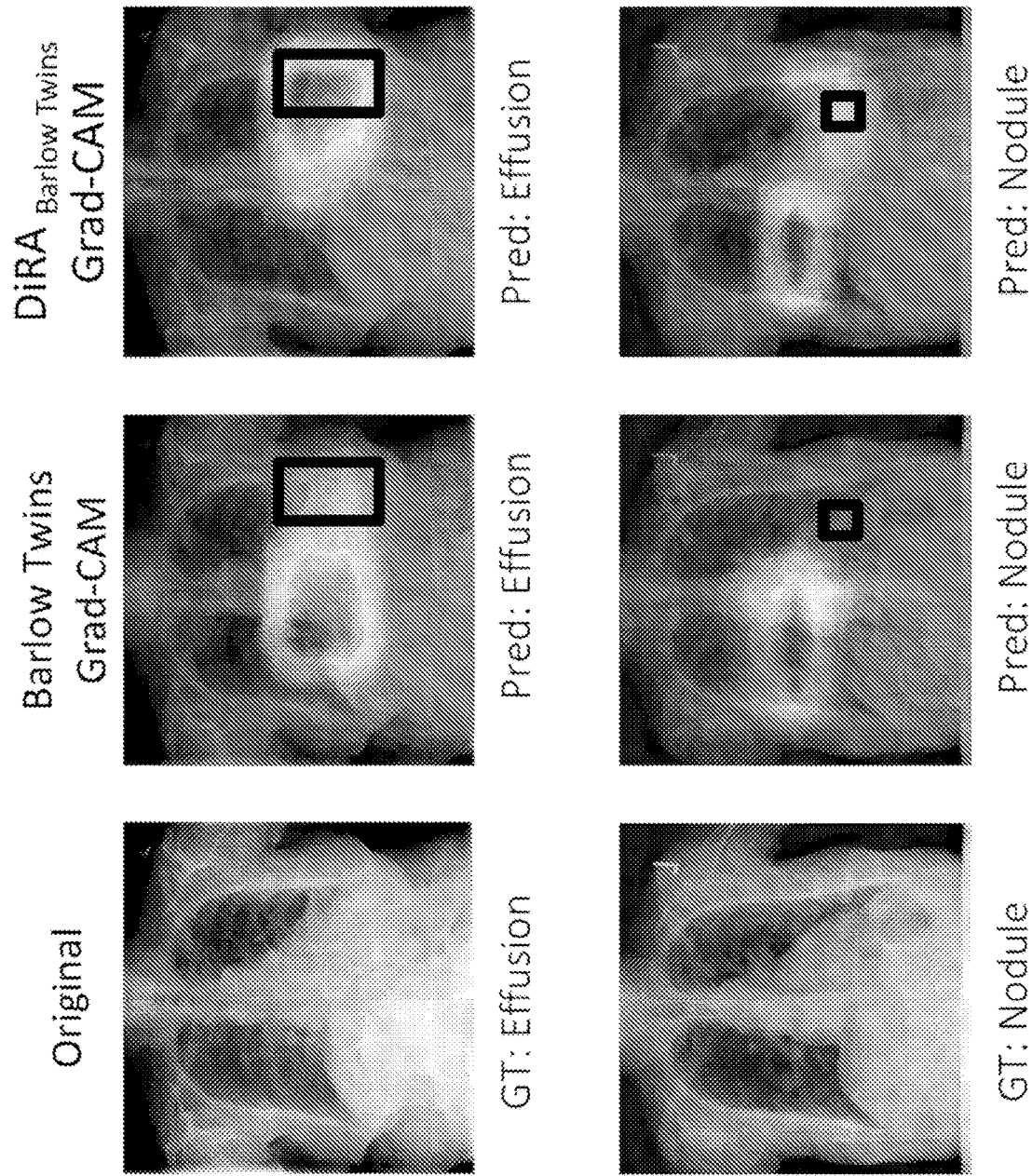
Figure 4C:
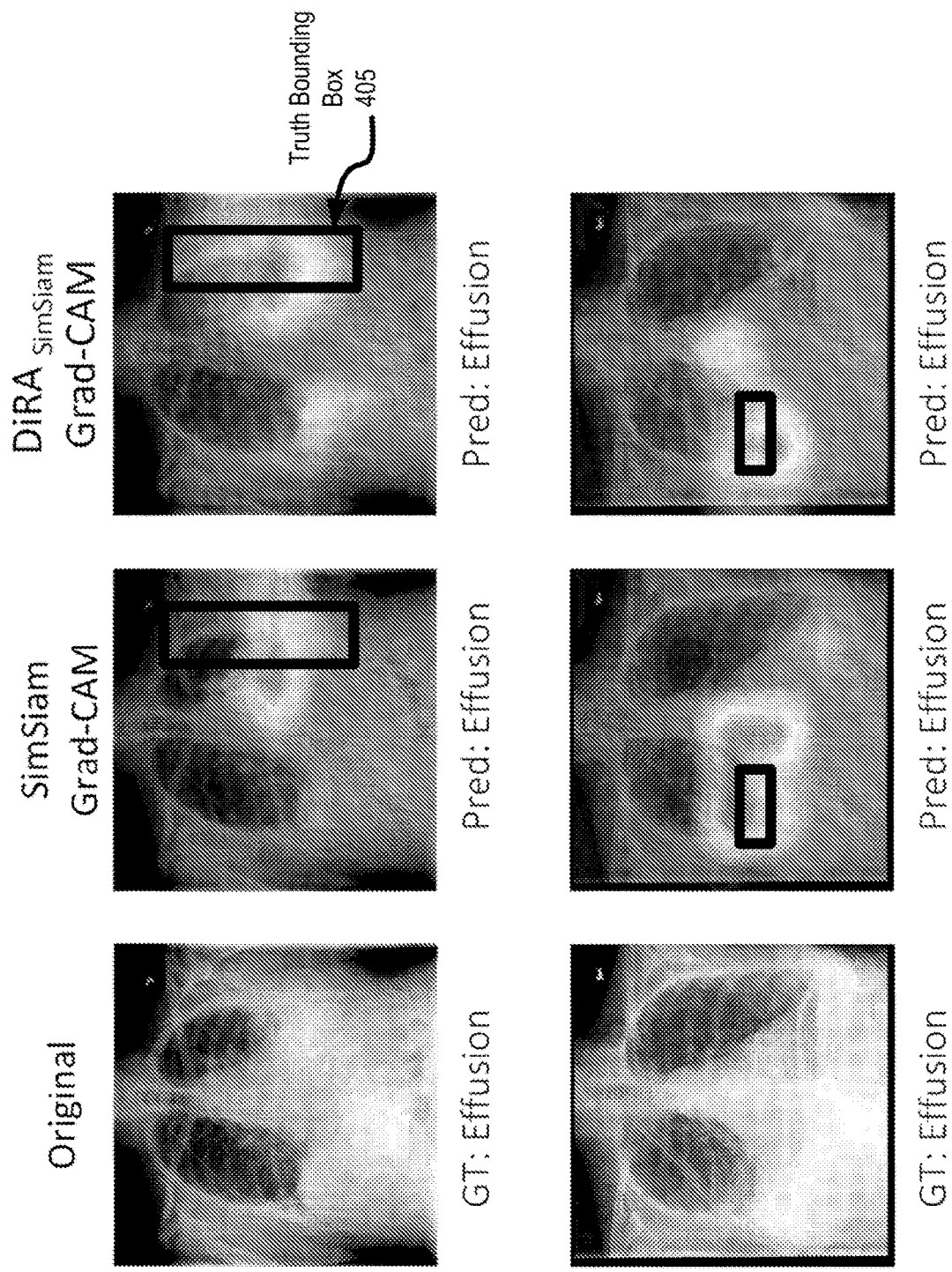

FIGS. 4A, 4B, and 4C provide visualizations of Grad-CAM heatmaps for (a) MoCo-v2 vs. $DiRA_{MoCo-v2}$, (b) Barlow Twins vs. $DiRA_{BarlowTwins}$, and (c) SimSiam vs. $DiRA_{SimSiam}$, in accordance with described embodiments.

The ground truth bounding box 405 annotations are shown via the bold rectangles overlaid onto the heatmaps. Training with DiRA leads to improvements in weakly-supervised disease localization. While both DiRA and underlying models predict the correct disease label on the test images, DiRA models capture the diseased locations more precisely than the baselines which attune to larger regions of the image (e.g., refer to FIG. 4C, second row) or provide inaccurate localization with no overlap with the ground truth (e.g., refer to FIG. 4B, second row).

DiRA Improves Weakly-Supervised Localization:

Experimental setup: Benefits of the DiRA framework were investigated experimentally in a weakly supervised setting, comparing its applicability for localizing chest pathology to underlying discriminative methods. Given this goal, the ChestX-ray14 dataset was utilized which contains bounding box annotations for approximately 1,000 images. For training, models were initialized with the DiRA pre-trained models, and downstream models were trained using only image-level disease labels. Bounding boxes were only used as ground truth to evaluate disease localization accuracy in the testing phase. To generate heatmaps, Grad-CAM was leveraged. The heatmaps depicted at each of FIGS. 4A, 4B, and 4C indicate the spatial location of a particular thoracic disease.

Results: As seen in FIGS. 4A, 4B, and 4C, the DiRA framework learns more fine-grained representations, enabling it to localize diseases more accurately. In particular, heatmaps generated by MoCo-v2, Barlow Twins, and SimSiam models are highly variable, whereas the DiRA models as described herein consistently achieve more robust and accurate localization results over each corresponding original method. Through the production of more interpretable activation maps, the DiRA framework demonstrates possible clinical potential for post-hoc interpretation by radiologists. Quantitative disease localization results are discussed in greater detail below (refer to the discussion below in the context of FIGS. 5A, 5B, and 5C and also Table 5, as set forth at FIG. 2E, element 205, for details of each dataset).

DiRA Outperforms Fully-Supervised Baselines:

Experimental setup: Following the recent transfer learning benchmark in medical imaging, a comparison of the transferability of DiRA models was performed, pre-trained solely on unlabeled images from ChestX-ray14, with two fully-supervised representation learning approaches: (1) supervised ImageNet model, the most common transfer learning pipeline in medical imaging and (2) supervised model pretrained on ChestX-ray14, the upper-bound in-domain transfer learning baseline. The supervised baselines benefit from the same encoder as DiRA, namely ResNet-50. All pre-trained models were fine-tuned for 4 distinct medical applications ranging from target tasks on the source dataset to the tasks with comparatively significant domain-shifts in terms of data distribution and disease/object of interest.

Figure 2B:
FIG. 2B depicts Table 2 which depicts a comparison with fully-supervised transfer learning, in accordance with described embodiments.

FIG. 2B depicts Table 2 (element 202) which depicts a comparison with fully-supervised transfer learning, in accordance with described embodiments.

As shown here, DiRA models outperform fully-supervised pre-trained models on ImageNet and ChestX-ray14 in three downstream tasks. The best methods are bolded while the second best are underlined. The squared and non-squared upward arrows † and ‡ present the statistically significant (p<0.05) improvement compared with supervised ImageNet and ChestX-ray14 baselines, respectively, while the symbols * and + present the statistically equivalent performances accordingly. For the supervised ChestX-ray14 model, transfer learning to ChestXray14 is not applicable since pre-training and downstream tasks are the same, denoted by the dash symbol "-".

Results: As seen in Table 2 as set forth at FIG. 2B, element 202, the DiRA models achieve significantly better or on-par performance compared with both supervised ImageNet and ChestX-ray14 models across four downstream tasks. In particular, $DiRA_{MoCo-v2}$ and $DiRA_{Barlow\ Twins}$ outperforms both supervised baselines in CheXpert, SIIM-ACR, and Montgomery, respectively. Moreover, $DiRA_{SimSiam}$ outperforms the supervised ImageNet and the ChestX-ray14 pre-trained models in SIIMACR and Montgomery, respectively. These results indicate that the disclosed DiRA framework, with zero annotated data, is capable of providing more generic features for different medical tasks.

DiRA Sets a New State-of-the-Art for Self-Supervised Learning in 3D Medical Imaging:

Experimental setup: Further investigated was the effectiveness of the disclosed DiRA framework for enhancing restorative representation learning by applying DiRA to TransVW, the prior state-of-the-art SSL approach for 3D medical imaging. Specifically, TransVW was selected as representative of restorative self-supervised methods because it shows superior performance over discriminative, restorative only, and restorative and adversarial methods. Following a common evaluation pipeline, learned representations were evaluated by transfer learning to five common and challenging 3D downstream tasks, including classification (LUNA and PE-CAD) and segmentation (LIDC, LiTS, and BraTS).

FIG. 2C depicts Table 3 (element 203) which depicts a comparison with a restorative self-supervised method, in accordance with described embodiments.

As shown here, the DiRA platform and methodology as described herein is applied to the Trans VW methodology as the SOTA restorative self-supervised method. As shown, DiRA enhances TransVW by conserving more fine-grained details, resulting in performance boosts in four 3D downstream tasks.

Results: As seen in Table 3 as set forth at FIG. 2C, element 203, the DiRA framework consistently enhances TransVW across all downstream tasks. In particular, the DiRA framework improved Trans VW in LUNA, LIDC-IDRI, LiTS, and BraTS, and offers equivalent performance in PE-CAD. These results imply that by utilizing three learning components in tandem, image-based self-supervision approaches capture a more diverse visual representation that generalizes better to different downstream tasks.

Ablation study-Experimental setup: A thorough ablation study was further conducted to show experimentally how each component contributes to the DiRA framework. To do so, only the loss function of DiRA was varied. For each underlying self-supervised method, (e.g., such as MoCo-v2, Barlow Twins, and SimSiam, referred to as the base), the experiment started with the discrimination component and incrementally added the restorative learning component and the adversarial learning component. When all three components are unified, they represent the completed DiRA models as described herein. All models were pretrained on the ChestX-ray14 dataset and fine-tuned for four downstream tasks, including ChestX-ray14, CheXpert, SIIM-ACR, and Montgomery.

Figure 2D:
FIG. 2D depicts Table 4 which depicts an ablation study on different components of DiRA, in accordance with described embodiments.

FIG. 2D depicts Table 4 (element 204) which depicts an ablation study on different components of DiRA, in accordance with described embodiments.

As shown here, the impact of each component of DiRA is studied, including discrimination, restoration, and adversary, in four downstream tasks. Adding restorative learning ($L_{res}$) to discriminative learning leads to consistent performance improvements as depicted by the results annotated with the upward arrow symbol (↑). Furthermore, equipping models with adversarial learning ($L_{adv}$) yields performance boosts across all tasks.

Results: Observations are drawn from the results as seen in Table 4 as set forth at FIG. 2D, element 204. Specifically observed are the following: Firstly, (1) expanding discriminative self-supervised methods by adding a restoration task consistently enhances the original methods. In particular, incorporating $L_{res}$ into training objectives of MoCo-v2, Barlow Twins, and SimSiam outperforms the corresponding original methods, with the exception of SimSiam in ChestXray14, which shows slight performance degradation. Note that this gap later compensates and results in an overall improvement after adding $L_{adv}$, which signifies collaborative learning among restorative and adversary components through the use of the disclosed DiRA framework. Secondly, (2) the overall trend showcases the advantage of the adversarial discriminator when added to the restoration component, improving the performance of all methods in four downstream tasks. The experimental results shown here indicate that unifying the three components via the disclosed DiRA models significantly enhances the original self-supervised methods by retaining more fine-grained information from images.

Figure 5A:
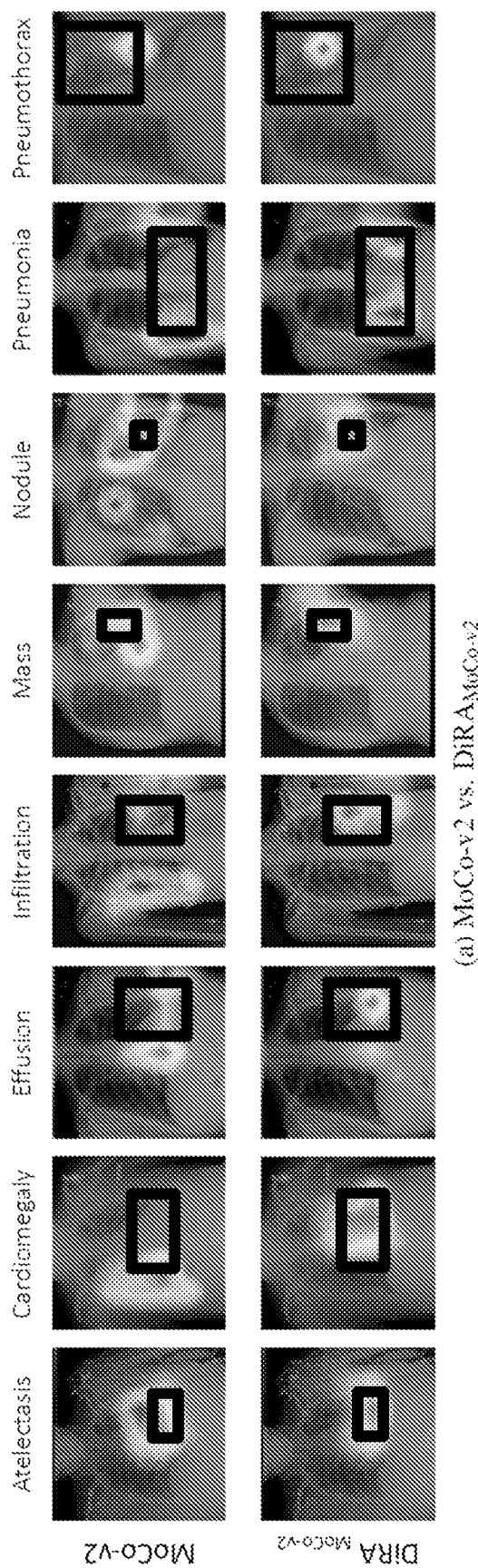
FIGS. 5A, 5B, and 5C provide visualizations of Grad-CAM heatmaps examples for 8 thorax diseases in each column, according to described embodiments.
Figure 5B:
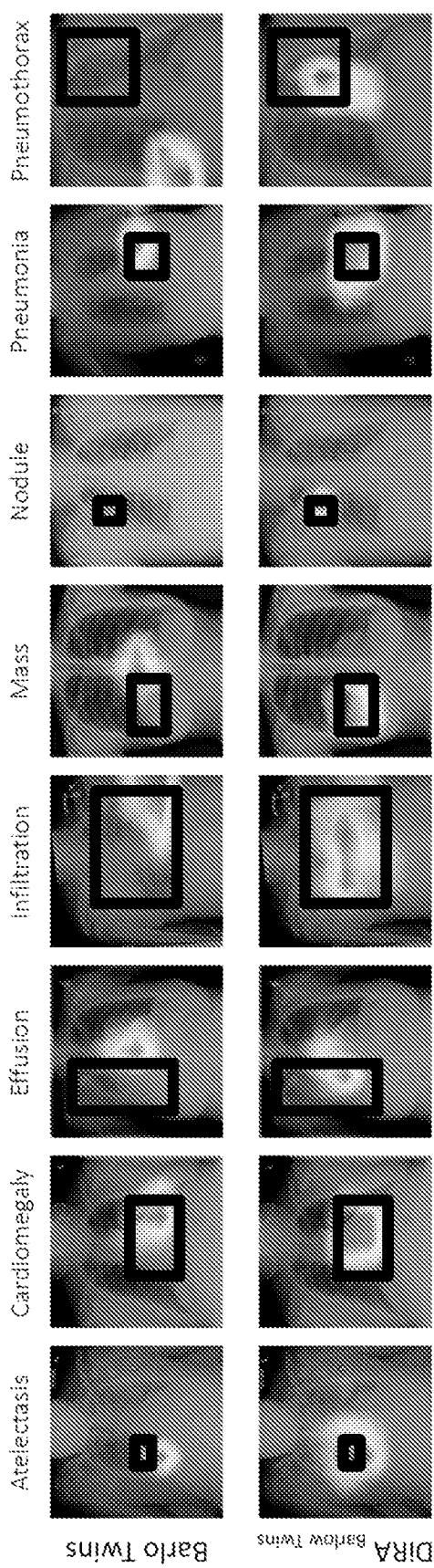
Figure 5C:
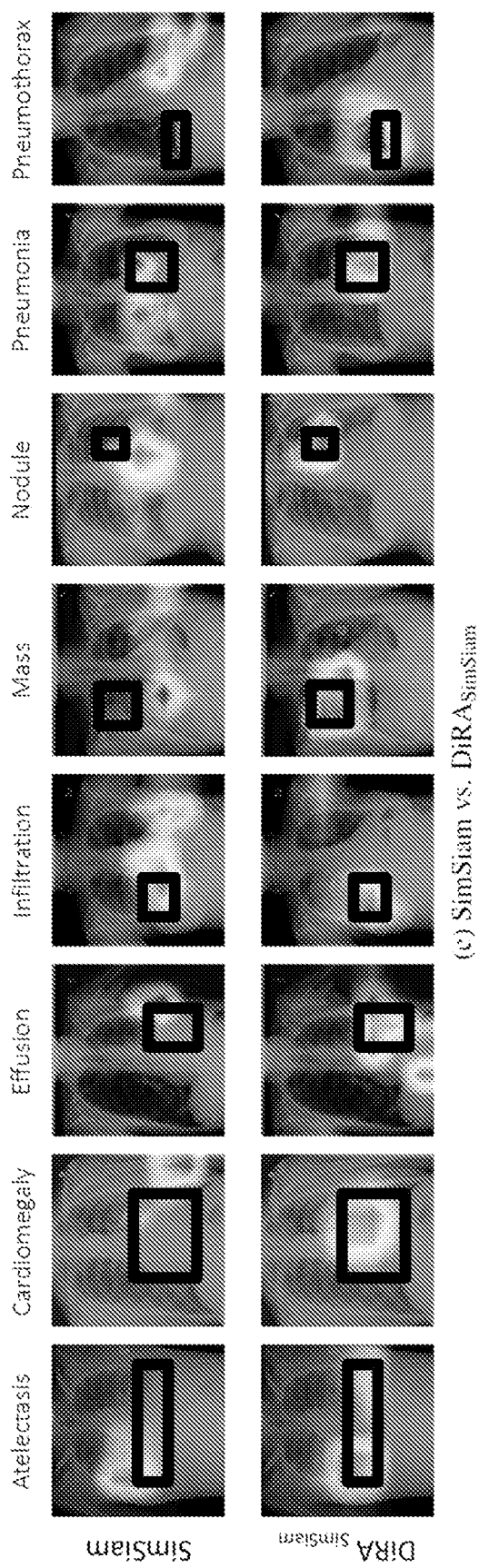

FIGS. 5A, 5B, and 5C provide visualizations of Grad-CAM heatmaps examples for 8 thorax diseases in each column, according to described embodiments.

The first row in each of FIGS. 5A, 5B, and 5C represents the results for the original self-supervised method, while the second row represents the original method when adopted in the disclosed DiRA framework. The thick black boxes represent the localization ground truths.

Weakly-Supervised Localization:

Additional quantitative results and additional qualitative results for weakly-supervised localization are provided here, further to the discussion above. Specifically, the quantitative results provided by Table 5 as set forth at FIG. 2E, element 205, together with the qualitative results in Table 5 and FIG. 5, demonstrate the capability of the disclosed DiRA framework in learning fine-grained representations that can be used for more accurate pathology localization when just image-level annotations are available.

QUANTITATIVE—Experimental setup: Following a common protocol, applicability of the disclosed DiRA framework was quantitatively evaluated in a weakly supervised setting using ChestX-ray14 dataset. First, min-max normalization was used to normalize each heatmap; then the heatmaps were binarized by thresholding at {60, 180}, and bounding boxes were generated around the isolated regions. To evaluate localization accuracy, the intersection over union (IoU) was calculated between the generated and ground truth bounding boxes. According to accepted principals, a localization is correct when the bounding box prediction overlaps with the ground truth box with IoU≥δ. The accuracy of localization under various δ values was then evaluated, from 10% to 60%. Each method was run ten times and the average accuracy across all runs was reported.

Figure 2E:
FIG. 2E depicts Table 5 which depicts weakly-supervised pathology localization accuracy under different IoU thresholds ($\delta$), in accordance with described embodiments.

FIG. 2E depicts Table 5 (element 205) which depicts weakly-supervised pathology localization accuracy under different IoU thresholds (δ), in accordance with described embodiments.

As shown here, the DiRA models provide stronger representations for pathology localization with only image-level annotations. For each method, the average performance is reported over ten runs. The results annotated by the upward arrow symbol (↑) show the improvement of DiRA models compared with the underlying discriminative method in each IoU threshold.

QUANTITATIVE-Results: The data at Table 5 (FIG. 2E, element 205), shows the pathology localization accuracy of the disclosed DiRA framework and the underlying discriminative models. As seen, in each of the six IoU thresholds, the DiRA models significantly outperform the corresponding discriminative models. In particular, the average of improvement for MoCo-v2, Barlow Twins, and SimSiam across all IoU thresholds is 2.38%, 5.4%, and 9.4%, respectively.

QUALITATIVE—Experimental setup: During training, the models were initialized using the DiRA pre-trained models, and downstream models were fine-tuned using only image-level disease labels. Heatmaps were used to approximate the spatial location of a particular thorax disease. The heatmaps were generated using Grad-CAM, which is a technique for highlighting the important regions in the image for predicting the pathology class.

QUALITATIVE—Results: The images shown at FIG. 5 present the visualizations of heatmaps generated by DiRA and the corresponding discriminative models for 8 thorax pathologies in ChestX-ray14 dataset. As shown here, DiRA models provide more accurate pathology localizations compared to the underlying discriminative methods. These results demonstrate the impact of restorative learning in providing fine-grained features that are useful for disease localization.

Datasets and Tasks:

Through experimentation, the disclosed DiRA framework was examined across a diverse suite of 9 downstream tasks, including classification and segmentation in X-ray, CT, and MRI modalities. In this section, the details of each dataset and the underlying task are provided, as well as the evaluation metric for each task.

ChestX-ray14: ChestX-ray14 is a large open-source dataset of pre-identified chest X-ray images. The dataset includes 112K chest images taken from 30K unique patients. The ground truth consists of a label space of 14 thorax diseases. The inventors used the official patient-wise split released with the dataset, including 86K training images and 25K testing images. The models are trained to predict 14 pathologies in a multi-label classification setting. The mean AUC score over 14 diseases is used to evaluate the classification performance. In addition to image-level labels, ChestX-ray14 provides bounding box annotations for approximately 1,000 test images. Of this set of images, bounding box annotations are available for eight (8) out of 14 thorax diseases. During testing, bounding box annotations were used to assess the accuracy of pathology localization in a weakly-supervised setting. The mean accuracy over eight (8) diseases is used to evaluate the localization performance.

CheXpert: CheXpert is a hospital-scale publicly available dataset with 224K chest X-ray images taken from 65K unique patients. The inventors used the official data split released with the dataset, including 224K training and 234 test images. The ground truth for the training set includes 14 thoracic pathologies that were retrieved automatically from radiology reports. The testing set is labeled manually by board-certified radiologists for five (5) selected thoracic pathologies—Cardiomegaly, Edema, Consolidation, Atelectasis, and Pleural Effusion. The models are trained to predict five pathologies in a multi-label classification setting. The mean AUC score over five (5) diseases is used to evaluate the classification performance.

SIIM-ACR: This open dataset is provided by the Society for Imaging Informatics in Medicine (SIIM) and the American College of Radiology, including 10K chest X-ray images and pixel-wise segmentation mask for Pneumothorax disease. The dataset was randomly divided into training (80%) and testing (20%) sub-sets. The models are trained to segment pneumothorax from chest radiographic images (if present). The segmentation performance was measured by the mean Dice coefficient score.

NIH Montgomery: This publicly available dataset is provided by the Montgomery County's Tuberculosis screening program, including 138 chest X-ray images. There are 80 normal cases and 58 cases with Tuberculosis (TB) indications in this dataset. Moreover, ground truth segmentation masks for left and right lungs are provided. The dataset was randomly divided into a training set (80%) and a test set (20%). The models were trained to segment left and right lungs in chest scans. The segmentation performance was evaluated by the mean Dice score.

LUNA: This publicly available dataset consists of 888 lung CT scans with a slice thickness of less than 2.5 mm. The dataset was divided into training (445 cases), validation (178 cases), and test (265 cases) sets. The dataset provides a set of 5M candidate locations for lung nodule. Each location is labeled as true positive (1) or false positive (0). The models are trained to classify lung nodule candidates into true positives and false positives in a binary classification setting. The classification accuracy was evaluated by Area Under the Curve (AUC) score.

PE-CAD: This dataset includes 121 computed tomography pulmonary angiography (CTPA) scans with a total of 326 pulmonary embolism (PE). The dataset provides a set of candidate locations for PE and is divided at the patient-level into training and test sets. Training set contains 434 true positive PE candidates and 3,406 false positive PE candidates. Test set contains 253 true positive PE candidates and 2,162 false positive PE candidates. The 3D scans were pre-processed. The 3D models were trained to classify PE candidates into true positives and false positives in a binary classification setting. The classification accuracy was evaluated by Area Under the Curve (AUC) score at candidate-level.

LIDC-IDRI: The Lung Image Database Consortium image collection (LIDC-IDRI) dataset is created by seven academic centers and eight medical imaging companies. The dataset includes 1,018 chest CT scans and marked-up annotated lung nodules. The dataset is divided into training (510), validation (100), and test (408) sets. The data was pre-processed by re-sampling the 3D volumes to 1-1-1 spacing and then extracting a 64×64×32 crop around each nodule. The models are trained to segment long nodules in these 3D crops. The segmentation accuracy is measured by the Intersection over Union (IoU) metric.

LiTS: The dataset is provided by MICCAI 2017 LiTS Challenge, including 130 CT scans with expert ground-truth segmentation masks for liver and tumor lesions. The dataset was divided into training (100 patients), validation (15 patients), and test (15 patients) sets. The models were trained to segment liver in 3D scans. The segmentation accuracy was measured by the Intersection over Union (IoU) metric.

BraTS: The dataset includes brain MRI scans of 285 patients (210 HGG and 75 LGG) and segmentation ground truth for necrotic and non-enhancing tumor core, peritumoral edema, GD-enhancing tumor, and background. For each patient, four different MR volumes are available: native T1-weighted (T1), post-contrast T1-weighted (T1Gd), T2-weighted (T2), and T2 fluid attenuated inversion recovery (FLAIR). The dataset was divided at the patient-level into training (190 patients) and testing (95 patients) sets. The models were trained to segment brain tumors (background as negatives class and tumor sub-regions as positive class). The segmentation accuracy is measured by the Intersection over Union (IoU) metric.

IMPLEMENTATION DETAILS-Pre-training settings: DiRA was applied to four existing self-supervised methods. To be self-contained, each method is explained briefly here. Additional pre-training details that supplement the above section entitled "Pre-training protocol" are provided, as follows.

MoCo-v2: The proposed implementation adopts MoCo-v2—a popular representative of contrastive learning methods, into the described framework. MoCo leverages a momentum encoder to ensure the consistency of negative samples as they evolve during training. Moreover, a queue $K=\{k_1, k_2, \ldots k_N\}$ is utilized to store the representations of negative samples. The discrimination task is to contrast representations of positive and negative samples. As MoCo-v2 is adopted into the DiRA framework, the encoder $f_\theta$ and projection head $h_\theta$ are updated by back-propagation, while $f_\epsilon$ and $h_\epsilon$ are updated by using an exponential moving average (EMA) of the parameters in $f_\theta$ and $h_\theta$, respectively.

The discrimination branch is trained using InfoNCE loss, which for a pair of positive samples $x_1$ and $x_2$, defined at equation (5), as follows:

$$\mathcal{L}_{dis} = -\log \frac{\exp(z_1 \cdot z_2/\tau)}{\sum_{n=0}^{N} \exp(z_1 \cdot k_n/\tau)}$$

where $z_1 = h_\theta(f_\theta(x_1))$ and $z_2 = h_\varepsilon(f_\varepsilon(x_2))$, t is a temperature hyperparameter, and N is the queue size. For the sake of these experiments, $f_\theta$ is a standard ResNet-50 and $h_\theta$ is a two-layer MLP head (hidden layer 2048-d, with ReLU). Moreover, when adopting MoCo-v2 in DiRA, $f_\theta$, $h_\theta$, and $g_\theta$, are optimized using SGD with an initial learning rate of 0.03, weight decay 0.0001, and the SGD momentum 0.9.

SimSiam: The proposed implementation further adopts SimSiam—a popular representative of asymmetric instance discrimination methods, into the described framework. SimSiam trains the model without negative pairs and directly maximizes the similarity of two views from an image using a simple siamese network followed by a predictor head. To prevent collapsing solutions, a stop-gradient operation is utilized. As such, the model parameters are only updated using one distorted version of the input, while the representations from another distorted version are used as a fixed target. As SimSiam is adopted in DiRA, the encoder $f_\theta$ and projection head $h_\theta$, share weights with $f_\varepsilon$ and $h_\varepsilon$, respectively. The model is trained to maximize the agreement between the representations of positive samples using negative cosine similarity, defined at equation (6), as follows:

$$\mathcal{D}(z_1, y_2) = -\frac{z_1}{\|z_1\|_2} \cdot \frac{y_2}{\|y_2\|_2}$$

where $z_1 = h_\theta(f_\theta(x_1))$ and $y_2 = f_\varepsilon(x_2)$.

The discrimination branch is trained using a symmetrized loss as set forth at equation (7), as follows:

$$\mathcal{L}_{dis} = \frac{1}{2} \mathcal{D}(z_1, stopgrad(y_2)) + \frac{1}{2} \mathcal{D}(z_2, stopgrad(y_1))$$

where stopgrad means that $y_2$ is treated as a constant in this term. For the sake of these experiments, $f_\theta$ is a standard ResNet-50 and $h_\theta$ is a three-layer projection MLP head (hidden layer 2048-d), followed by a two-layer predictor MLP head. Moreover, when adopting SimSiam in DiRA, $f_\theta$, $h_\theta$, and $g_\theta$, are optimized using SGD with a linear scaling learning rate (lr×BatchSize/256). The initial learning rate is 0.05, weight decay is 0.0001, and the SGD momentum is 0.9.

Barlow Twins: Still further, the proposed implementation adopts Barlow Twins—a popular representative of redundancy reduction instance discrimination learning methods, into the novel DiRA framework. Barlow Twins makes the cross-correlation matrix computed from two siamese branches close to the identity matrix. By equating the diagonal elements of the cross-correlation matrix to 1, the representation will be invariant to the distortions applied to the samples. By equating the off-diagonal elements of the cross-correlation matrix to 0, the different vector components of the representation will be decorrelated, so that the output units contain non-redundant information about the sample. The discrimination loss is defined at equation (8), as follows:

$$\mathcal{L}_{dis} = \sum_i (i - C_{ii})^2 + \lambda \sum_i \sum_{i \neq j} C_{ij}^2$$

where C is the cross-correlation matrix computed between the outputs of the $h_\theta$ and $h_\varepsilon$ networks along the batch dimension. $\lambda$ is a coefficient that determines the importance of the invariance term and redundancy reduction term in the loss. For the sake of these experiments, $f_\theta$ is a standard ResNet-50 and $h_\theta$ is a three-layer MLP head. Moreover, when adopting Barlow Twins in DiRA, $f_\theta$, $h_\theta$, and $g_\theta$, are optimized using LARS optimizer with a learning rate schedule successfully utilized in other experiments.

TransVW: TransVW defines the similar anatomical patterns within medical images as anatomical visual words, and combines the discrimination and restoration of visual words in a single loss objective. As TransVW is adopted in DiRA, the encoder $f_\theta$ and projection head $h_\theta$ are identical to $f_\varepsilon$ and $h_\varepsilon$, respectively. In particular, the discrimination branch is trained to classify instances of visual words according to their pseudo class labels using the standard cross-entropy loss, as set forth at equation (9), as follows:

$$\mathcal{L}_{dis} = -\frac{1}{B} \sum_{b=1}^{B} \sum_{c=1}^{C} y_{bc} \log \mathcal{P}_{bc}$$

where B denotes the batch size; C denotes the number of visual words classes; Y and P represent the ground truth (one-hot pseudo label vector obtained from visual word classes) and the prediction of $h_\theta$, respectively. For the sake of these experiments, 3D U-Net is used as the $f_\theta$ and $g_\theta$. $h_\theta$ includes a set of fully-connected layers followed by a classification head. The terms $f_\theta$ and $g_\theta$ are trained using similar setting as found to be successful in prior experiments.

Joint training process: The overall pre-training was performed with the discrimination, restoration, and adversarial losses in a gradual evolutionary manner. First, the encoder $f_\theta$ along with projector $h_\theta$ are optimized using the discrimination loss $L_{dis}$ according to the learning schedule of the existing discriminative methods, empowering the model with an initial discrimination ability. Then, the restoration and adversarial losses are further fused into the training process incrementally. To stabilize the adversarial training process and reduce the noise from imperfect restoration at initial epochs, the process first warm up the $f_\theta$ and $g_\theta$ using the $L_{dis} + L_{res}$, and then add the adversarial loss $L_{adv}$ to jointly train the whole framework; the optimization of the framework by incorporation of $L_{res}$ and $L_{adv}$ takes up to 800 epochs. For the sake of these experiments, the early-stop technique was used on the validation set, and the checkpoints with the lowest validation loss were used for fine-tuning.

Implementation Details—Fine-Tuning Settings:

Preprocessing and data augmentation: For the sake of these experiments, for 2D target tasks on X-ray datasets (ChestX-ray14, CheXpert, SIIM-ACR, and Montgomery), the images were re-sized to 224×224. For thorax diseases classification tasks on ChestX-ray14 and CheXpert, standard data augmentation techniques were applied, including random cropping and resizing, horizontal flipping, and rotating. For segmentation tasks on SIIM-ACR and Montgomery, random brightness contrast, random gamma, optical distortion, elastic transformation, and grid distortion were applied. For 3D target tasks, regular data augmentations were used including random flipping, transposing, rotating, and adding Gaussian noise.

Training parameters: The training objective is to optimize each downstream task with the best performing hyperparameters. In all 2D and 3D downstream tasks, Adam optimizer was used with $\beta_1=0.9$, $\beta_2=0.999$. An early-stop mechanism was implemented using the 10% of the training data as the validation set to avoid over-fitting. For 2D classification tasks on ChestX-ray14 and CheXpert datasets, a learning rate 2e-4 was used and ReduceLROnPlateau was used as the learning rate decay scheduler. For 2D segmentation tasks on SIIM-ACR and Montgomery, a learning rate 1e-3 was used and a cosine learning rate decay scheduler. For all 3D downstream tasks, ReduceLROnPlateau was used as the learning rate decay scheduler. For downstream tasks on LUNA, PECAD, LIDC, and LiTS, use a learning rate 1e-2 was used. For BraTS dataset, a learning rate of 1e-3 was used.

As discussed above, there are marked differences between medical and natural images. Medical imaging protocols are designed for defined clinical purposes by focusing on particular parts of the body, generating images of great similarity in anatomy across patients. For example, chest X-rays tend to look similar. By contrast, natural images, especially those in ImageNet, are largely object-centered, meaning objects of interest are at the center of the images with largely varying backgrounds. For instance, images for dogs and cats in the ImageNet dataset mostly have dogs and cats at the center, and their backgrounds may vary dramatically. Intuitively, these differences have impacts on the performance of discriminative learning, restorative learning, and adversarial learning applied to medical images and to natural images.

Discriminative learning (instance-based or cluster-based) utilizes encoders, by design, to collect features from whole images to cluster images from the same (pseudo) class and distinguish images from different (pseudo) classes; thereby it aims to learn high-level discriminative representations. Restorative learning aims to reconstruct original images from their distorted versions; naturally, it must focus on local visual patterns to enforce the model to conserve fine-grained information in images, leading to complementary representations when combined with discriminative learning. Adversarial learning aims to enhance the quality of reconstruction by restorative learning; as a result, it improves feature learning through restorative learning (refer again to Table 4 as set forth at FIG. 2D, element 204).

Consistent anatomical structures in medical images harbor rich semantics about human anatomy, thus restoring these anatomical structures offers a unique opportunity for deep semantic representation learning throughout entire images. However, natural images lack such patterns, and a learning method may distinguish natural images by using features extracted from backgrounds. Intuitively, features from backgrounds are not reliable as those from objects of interest. Therefore, it is believed that this is the reason behind the remarkable performance gain from restorative and adversarial learning for medical images.

Based on the analysis of the fundamental differences in performance between discriminative and generative SSL methods in computer vision and in medical imaging, the DiRA framework as described herein, provides a new and beneficial SSL framework, by uniting discriminative, restorative, and adversary learning in a unified manner to glean complementary visual information from unlabeled data for fine-grained representation learning. It is further demonstrated that such a framework considerably improves the capabilities of self-supervised learning methods in (a) transfer learning across organs, diseases, and modalities, (b) robustness in small data regimes, and (c) fine-grained lesion localization using only image-level annotation.

One important contribution of the disclosed DiRA framework and complementary experiments arises from the insights gained into the synergy of these three SSL approaches for collaborative learning. Given DiRA's generalizability, it is envisioned that the DiRA framework will facilitate a fundamental step towards developing universal representations for medical imaging. While the experimental results described herein focused on medical imaging, it is nevertheless envisioned that the disclosed DiRA framework will also provide outstanding performance for vision tasks that demand fine-grained details.

Figure 6:
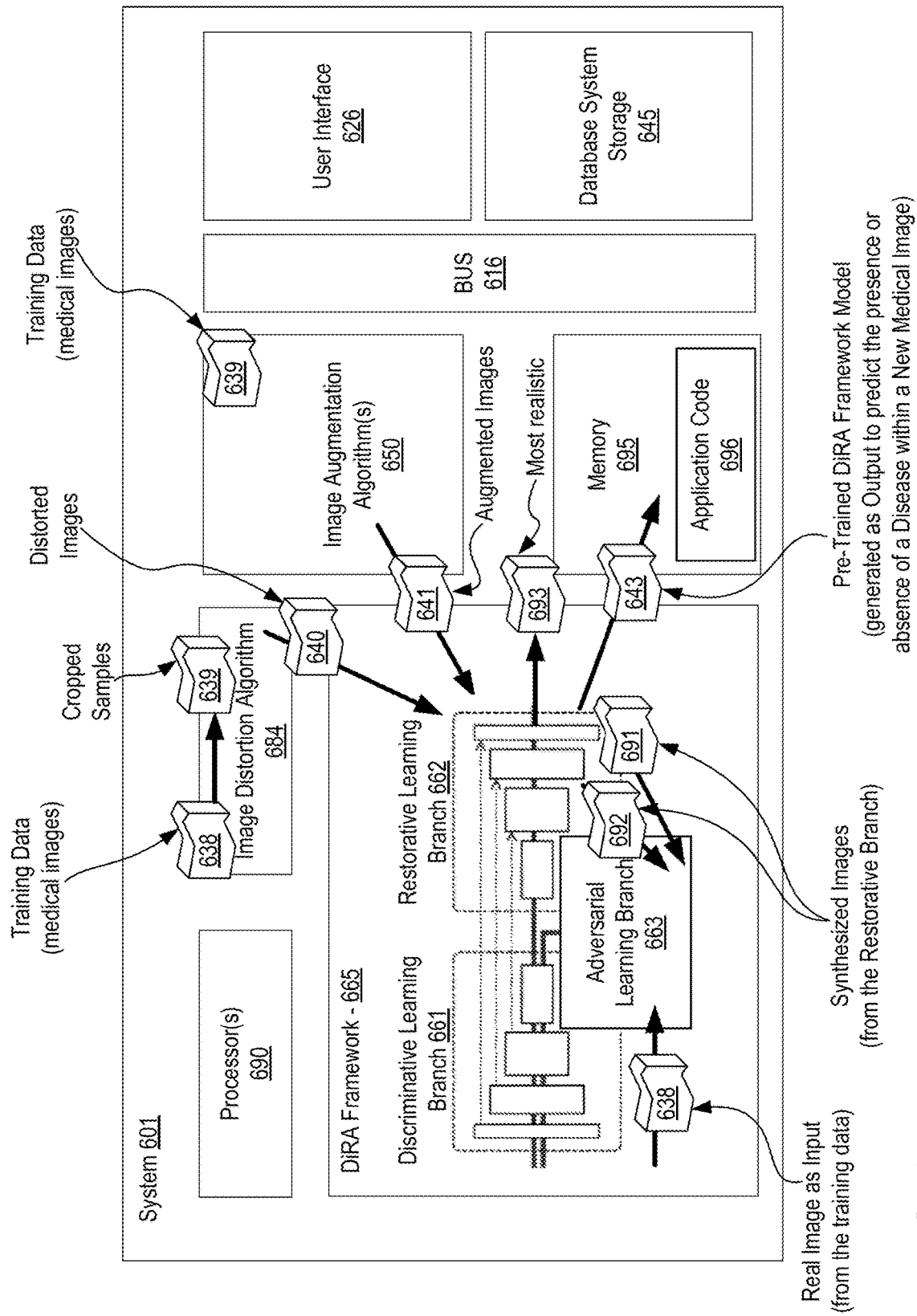
FIG. 6 shows a diagrammatic representation of a system within which embodiments may operate, be installed, integrated, or configured, in accordance with one embodiment.

FIG. 6 shows a diagrammatic representation of a system 601 within which embodiments may operate, be installed, integrated, or configured. In accordance with one embodiment, there is a system 601 having at least a processor 690 and a memory 695 therein to execute implementing application code 696. Such a system 601 may communicatively interface with and cooperatively execute with the benefit of remote systems, such as a user device sending instructions and data, a user device to receive as an output from the system 601 an especially pre-trained DiRA framework model 643 configured for medical diagnosis tasks on the basis of training data 638, distorted images 640 and augmented patches 641 from the original images. Further depicted is the pre-trained DiRA framework model 643 having been pre-trained using a combination of discriminative, restorative, and adversarial learning processes via which to process new medical images which form no part of the training data upon which the DiRA framework was trained.

According to the depicted embodiment, the system 601, includes a processor 690 and the memory 695 to execute instructions at the system 601. The system 601 as depicted here is specifically customized and configured to systematically generate the pre-trained DiRA Framework Model 643 which is generated as output to predict the presence or absence of a disease within a new medical image.

According to a particular embodiment, there is a specially configured system 601 which is custom configured to generate the pre-trained DiRA framework model 643 through the combined use of discriminative, restorative, and adversarial learning techniques. According to such an embodiment, the system 601 includes: a memory 695 to store instructions via executable application code 696; a processor 690 to execute the instructions stored in the memory 695; in which the system 601 is specially configured to execute the instructions stored in the memory via the processor which causes the system to receive training data 638 having a plurality of medical images therein at a framework for self-supervised medical image analysis via the application of a discriminative learning branch 661, a restorative learning branch 662, and an adversarial learning branch 663 of the depicted DiRA framework 665. For instance, the learning branch 662 is configured to restore and output the synthesized restorative image 693 as output which is gen evaluated by the adversarial learning branch 663 to determine if it is a realistic reproduction of a real training image. The system is further configured to crop two patches from the plurality of medical images to generate two cropped patches 639.

Further operations of the system include inputting the two cropped patches 639 into the restorative learning branch 662 form which the synthesized images (691 and 692) are generated.

The discriminative learning branch generates "discriminative latent features" from input images. Specifically, the discriminative learning branch 661 performs operations including: (i) receiving the two cropped patches 639, (ii) augmenting each of the two cropped patches via the image augmentation algorithms 650 to generate two augmented patches 641, and (iii) generating latent features from the two augmented patches 641 by training an encoder of the discriminative learning branch 661 to maximize agreement between instances of same classes in latent space via a discriminative loss function.

The system 601 further generates a synthesized restorative image 692 from the restorative learning branch 662 by: (i) receiving the two cropped patches 639, (ii) distorting each of the two cropped patches via the image distortion algorithm 684 to generate two distorted patches 640, (iii) training an encoder and decoder of the restorative learning branch 662 to map the two distorted patches 640 back to the two cropped patches 639 by minimizing a distance, at a pixel-level, between each original one of the two cropped patches 639 and a restored image generated by the restorative learning branch 662 corresponding to one of the medical images 638 from the training data or corresponding to one of the cropped patches 640 prior to having been distorted or augmented. The system then proceeds to output the synthesized restorative image 692 from the trained encoder and decoder of the restorative learning branch 662.

Further processing by the system includes the application of adversarial learning. In particular, the adversarial branch distinguishes the synthesized images generated by the restorative learning branch and the real images from the training data by executing an adversarial discriminator to perform a min-max function.

The system then outputs a pre-trained model 643 of the framework 665 based on the training of the discriminative learning branch and the training of the restorative learning branch and the training of the adversarial learning branch.

According to another embodiment of the system 601, a user interface 626 communicably interfaces with a user client device remote from the system and communicatively interfaces with the system via a public Internet.

Bus 616 interfaces the various components of the system 601 amongst each other, with any other peripheral(s) of the system 601, and with external components such as external network elements, other machines, client devices, the database system storage 645, cloud computing services, etc. Communications may further include communicating with external devices via a network interface over a LAN, WAN, or the public Internet.

Figure 7A:
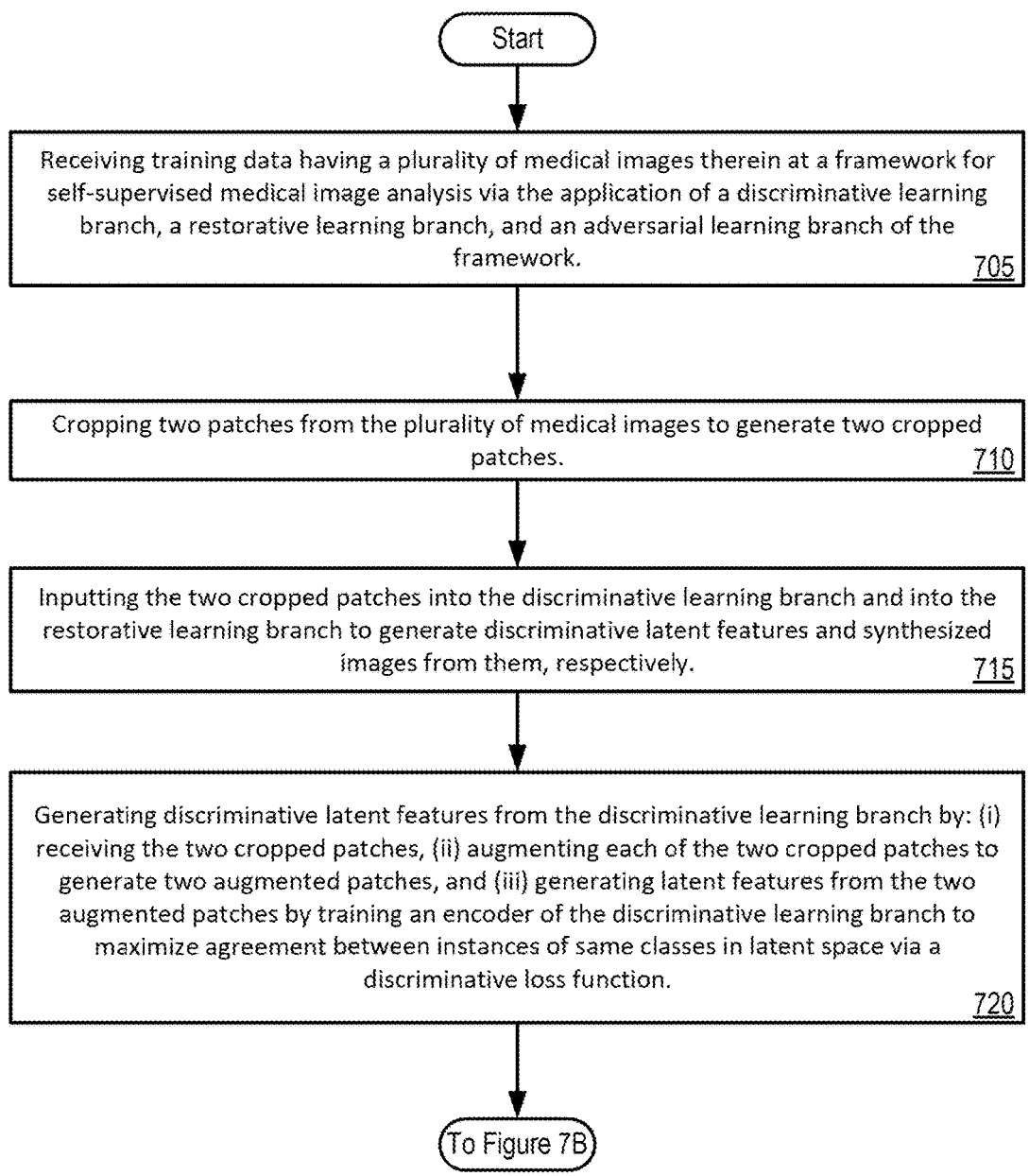
FIGS. 7A and 7B depict flow diagrams illustrating a method for implementing Discriminative, Restorative, and Adversarial (DiRA) learning for self-supervised medical image analysis, in accordance with one embodiment.
Figure 7B:
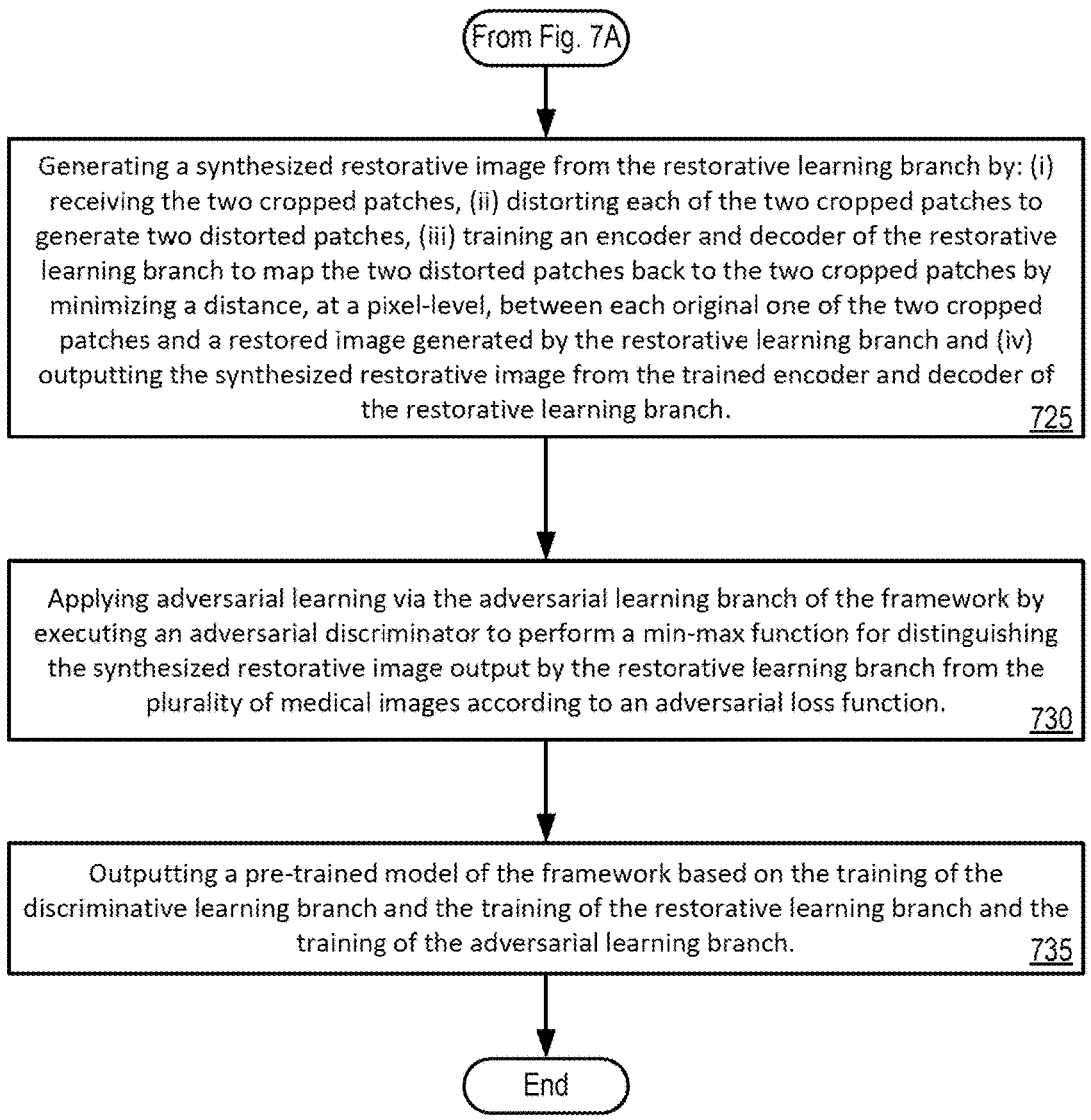

FIGS. 7A and 7B depict flow diagrams illustrating a method 700 and 701 for implementing Discriminative, Restorative, and Adversarial (DiRA) learning for self-supervised medical image analysis, in the context of processing of medical imaging. Method 700 and 701 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 601 (see FIG. 6) and the machine 801 (see FIG. 8) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 700 depicted at FIG. 7A, there is a method performed by a system specially configured for systematically implementing a DiRA Framework for learning for self-supervised medical image analysis, in accordance with disclosed embodiments. Such a system may be configured with at least a processor and a memory to execute specialized instructions which cause the system to perform the following operations:

At block 705, processing logic of such a system receives training data having a plurality of medical images therein at a framework for self-supervised medical image analysis via the application of a discriminative learning branch, a restorative learning branch, and an adversarial learning branch of the framework.

At block 710, processing logic crops two patches from the plurality of medical images to generate two cropped patches.

At block 715, processing logic inputs the two cropped patches into the discriminative learning branch and into the restorative learning branch to generate discriminative latent features and synthesized images from them, respectively.

At block 720, the discriminative learning branch generates "high-level latent features" from input images by: (i) receiving the two cropped patches, (ii) augmenting each of the two cropped patches to generate two augmented patches, (iii) generating the latent features from the two augmented patches, and training an encoder of the discriminative learning branch to maximize agreement between instances of same classes in latent space via a discriminative loss function.

With reference to the method 701 depicted at FIG. 7B, the method continues from the flow diagram as presented at FIG. 7A, with processing logic at block 725 generating a synthesized restorative image from the restorative learning branch by: (i) receiving the two cropped patches, (ii) distorting each of the two cropped patches to generate two distorted patches, (iii) training an encoder and decoder of the restorative learning branch to map the two distorted patches back to the two cropped patches by minimizing a distance, at a pixel-level, between each original one of the two cropped patches and a restored image generated by the restorative learning branch and (iv) outputting the synthesized restorative image from the trained encoder and decoder of the restorative learning branch.

At block 730, processing logic applies adversarial learning via the adversarial learning branch of the framework. In particular, the adversarial branch distinguishes the synthesized images generated by the restorative learning branch and the real images from the training data by executing an adversarial discriminator to perform a min-max function.

At block 735, processing logic outputs a pre-trained model of the framework based on the training of the discriminative learning branch and the training of the restorative learning branch and the training of the adversarial learning branch.

According to another embodiment of method 700-701, the framework implements a Discriminative, Restorative, and Adversarial learning framework (DiRA framework) for applying the pre-trained model of the framework to diagnosis and detection of a new medical image which forms no part of the training data received by the framework.

According to another embodiment of method 700-701, the pre-trained model of the framework is to render a prediction as to presence or absence of a disease within the new medical image and output the prediction as a predictive medical diagnosis for a medical patient.

According to another embodiment of method 700-701, cropping the two patches from the plurality of medical images incudes either (i) cropping both of the two patches from a single one of the plurality of medical images received; or alternatively, (ii) cropping one of the two patches from a first image and a second of the two patches from a second image, among the plurality of medical images received.

According to another embodiment of method 700-701, the synthesized images which are provided as output from the restorative branch are provided as input to the adversarial branch along with the real images from the training data being provided as input to the adversarial branch. The adversarial branch then operates to distinguish the synthesized images from the real images.

According to another embodiment of method 700-701, augmenting each of the two patches at the discriminative learning branch includes applying an augmentation function $T(\bullet)$ to generate the two augmented patches at the discriminative learning branch.

According to another embodiment of method 700-701, applying the discriminative learning via the discriminative learning branch comprises processing the two augmented patches at the discriminative learning branch through encoder networks $f_\theta$ and $f_\varepsilon$ of the discriminative learning branch configured for generating latent features $y_1=f_\theta(T(x_1))$ and $y_2=f_\varepsilon(T(x_2))$.

According to another embodiment of method 700-701, applying the discriminative learning via the discriminative learning branch further comprises projecting the latent features generated to a unit sphere via projection heads $h_\theta$ and $h_\varepsilon$ of the discriminative learning branch configured for outputting projections $z_1=h_{74}(y_1)$ and $z_2=h_\varepsilon(y_2)$.

According to another embodiment of method 700-701, the two cropped patches received as input at each of the discriminative learning branch and the restorative learning branch are received as identical inputs.

According to another embodiment of method 700-701, the discriminative learning branch includes: an augmentation function $T(\bullet)$ to generate the augmented patches via perturbation; twin encoders $f_\theta$ and $f_\varepsilon$ configured to generate the latent features; and projectors $h_\theta$ and $h_\varepsilon$ configured to project the latent features to a unit sphere and provide as output projections derived from the latent features.

According to another embodiment of method 700-701, the restorative learning branch includes: an encoder $f_\theta$ and decoder $g_\theta$ configured for mapping the augmented patches distorted by the augmentation function back to an original image via $f_\theta$, $g_\theta:(x,T) \mapsto x$; wherein the encoder $f_\theta$ of the restorative learning branch is a shared encoder, shared with the discriminative learning branch; and wherein the encoder $f_\theta$ and decoder $g_\theta$ comprise an encoder/decoder network trained by maximizing a distance at pixel-level between (i) an original sample corresponding to one of the cropped patches prior to processing by the augmentation function and (ii) a restored image generated by the restorative learning branch.

According to another embodiment of method 700-701, generating the discriminative latent features by training an encoder of the discriminative learning branch to maximize agreement between instances of a same class in a latent space via a discriminative loss function, includes one of: considering every single image amongst the plurality of medical images as a class using instance discrimination; or clustering images amongst the plurality of medical images based on a similarity metric using cluster discrimination.

According to another embodiment of method 700-701, the two patches cropped and inputted into the discriminative learning branch include two distinct views of one identical image or two different samples from an identical cluster of images.

According to another embodiment of method 700-701, generating the discriminative latent features from the discriminative learning branch includes: instantiating an $L_{dis}$ function utilizing one or more of cross-entropy discrimination learning, contrastive learning, redundancy reduction learning.

According to another embodiment of method 700-701, the $L_{dis}$ function is configurable by an end-user to select different types of discrimination tasks without constraint via the discrimination learning branch.

According to another embodiment of method 700-701, the restorative learning branch further generates fine-grained visual information at the restorative learning branch to supplement the latent features generated by the discriminative learning branch.

According to another embodiment of method 700-701, the adversarial learning branch reinforces a common network encoder shared by the discriminative learning branch and the restorative learning branch by jointly optimizing the common network encoder using the adversarial loss function of the adversarial learning branch to distinguish whether the synthesized restorative image output by the restorative learning branch is a realistic reproduction of a real training image.

According to another embodiment of method 700-701, the discriminative learning branch augments each of the two cropped patches via an image augmentation function $T(\bullet)$ which includes one or more of random horizontal flipping, color jittering, and Gaussian blurring of the two cropped patches.

According to another embodiment of method 700-701, each of the two cropped patches are further distorted by applying cutout and shuffling operations on the two cropped patches to make the restorative learning more challenging.

According to a particular embodiment, there is a non-transitory computer-readable storage medium having instructions stored thereupon that, when executed by a system having at least a processor and a memory therein, the instructions cause the processor to perform operations including: receiving training data having a plurality of medical images therein at a framework for self-supervised medical image analysis via the application of a discriminative learning branch, a restorative learning branch, and an adversarial learning branch of the framework; cropping two patches from the plurality of medical images to generate two cropped patches; inputting the two cropped patches into the discriminative learning branch and into the restorative learning branch to generate discriminative latent features and synthesized images from them, respectively; generating discriminative latent features from the discriminative learning branch by: (i) receiving the two cropped patches, (ii) augmenting each of the two cropped patches to generate two augmented patches, (iii) generating latent features from the two augmented patches by training an encoder of the discriminative learning branch to maximize agreement between instances of same classes in latent space via a discriminative loss function; generating a synthesized restorative image from the restorative learning branch by: (i) receiving the two cropped patches, (ii) distorting each of the two cropped patches to generate two distorted patches, (iii) training an encoder and decoder of the restorative learning branch to map the two distorted patches back to the two cropped patches by minimizing a distance, at a pixel-level, between each original one of the two cropped patches and a restored image generated by the restorative learning branch and (iv) outputting the synthesized restorative image from the trained encoder and decoder of the restorative learning branch; applying adversarial learning via the adversarial learning branch of the framework by executing an adversarial discriminator to perform a min-max function for distinguishing the synthesized restorative image output by the restorative learning branch from the plurality of medical images according to an adversarial loss function; and outputting a pre-trained model of the framework based on the training of the discriminative learning branch and the training of the restorative learning branch and the training of the adversarial learning branch.

Figure 8:
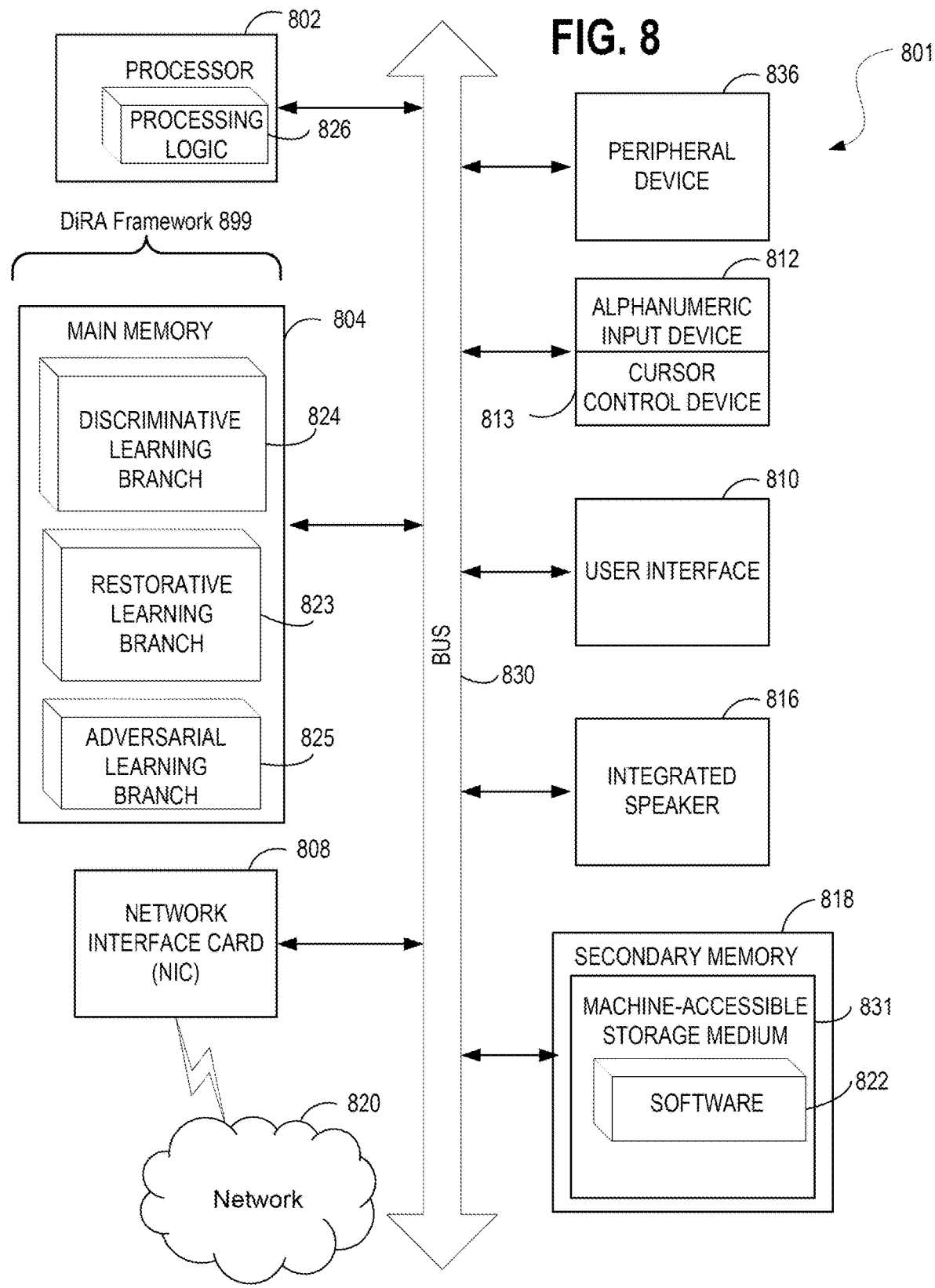
FIG. 8 illustrates a diagrammatic representation of a machine in the exemplary form of a computer system, in accordance with one embodiment.

FIG. 8 illustrates a diagrammatic representation of a machine 801 in the exemplary form of a computer system, in accordance with one embodiment, within which a set of instructions, for causing the machine/computer system to perform any one or more of the methodologies discussed herein, may be executed.

In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary machine 801 includes a processor 802, a main memory 804 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 818 (e.g., a persistent storage device including hard disk drives and a persistent database and/or a multi-tenant database implementation), which communicate with each other via a bus 830. Main memory 804 includes instructions for executing the various components of the DiRA Framework 899 as described herein, including the discriminative learning branch 824, the restorative learning branch 823, and the adversarial learning branch 825, in support of the methodologies and techniques described herein. Main memory 804 and its sub-elements are further operable in conjunction with processing logic 826 and processor 802 to perform the methodologies discussed herein.

Processor 802 represents one or more specialized and specifically configured processing devices such as a microprocessor, central processing unit, or the like. More particularly, the processor 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 802 may also be one or more special-purpose processing devices such as an application-specific integrated circuit (ASIC), a field programmable gate array (FPGA), a digital signal processor (DSP), network processor, or the like. Processor 802 is configured to execute the processing logic 826 for performing the operations and functionality which is discussed herein.

The machine 801 may further include a network interface card 808. The machine 801 also may include a user interface 810 (such as a video display unit, a liquid crystal display, etc.), an alphanumeric input device 812 (e.g., a keyboard), a cursor control device 813 (e.g., a mouse), and a signal generation device 816 (e.g., an integrated speaker). The machine 801 or computer system may further include peripheral device 836 (e.g., wireless or wired communication devices, memory devices, storage devices, audio processing devices, video processing devices, etc.).

The secondary memory 818 may include a non-transitory machine-readable storage medium or a non-transitory computer readable storage medium or a non-transitory machine-accessible storage medium 831 on which is stored one or more sets of instructions (e.g., software 822) embodying any one or more of the methodologies or functions described herein. The software 822 may also reside, completely or at least partially, within the main memory 804 and/or within the processor 802 during execution thereof by the machine 801, the main memory 804 and the processor 802 also constituting machine-readable storage media. The software 822 may further be transmitted or received over a network 820 via the network interface card 808.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A system comprising:
    a memory to store instructions;
    a set of one or more processors;
    a non-transitory machine-readable storage medium that provides instructions that, when executed by the set of one or more processors, the instructions stored in the memory are configurable to cause the system to perform operations comprising:
    receiving training data having a plurality of medical images therein at a framework for self-supervised medical image analysis via the application of a discriminative learning branch, a restorative learning branch, and an adversarial learning branch of the framework;

cropping two patches from the plurality of medical images to generate two cropped patches;

inputting the two cropped patches into the discriminative learning branch and into the restorative learning branch to generate discriminative latent features and synthesized images from them, respectively;

generating discriminative latent features from the discriminative learning branch by: (i) receiving the two cropped patches, (ii) augmenting each of the two cropped patches to generate two augmented patches, (iii) generating latent features from the two augmented patches by training an encoder of the discriminative learning branch to maximize agreement between instances of same classes in latent space via a discriminative loss function;

generating a synthesized restorative image from the restorative learning branch by: (i) receiving the two cropped patches, (ii) distorting each of the two cropped patches to generate two distorted patches, (iii) training an encoder and decoder of the restorative learning branch to map the two distorted patches back to the two cropped patches by minimizing a distance, at a pixel-level, between each original one of the two cropped patches and a restored image generated by the restorative learning branch and (iv) outputting the synthesized restorative image from the trained encoder and decoder of the restorative learning branch;

applying adversarial learning via the adversarial learning branch of the framework by executing an adversarial discriminator to perform a min-max function for distinguishing the synthesized restorative image output by the restorative learning branch from the plurality of real medical images according to an adversarial loss function; and outputting a pre-trained model of the framework based on the training of the discriminative learning branch and the training of the restorative learning branch and the training of the adversarial learning branch.

2. The system of claim 1, wherein the framework for self-supervised medical image analysis via the application of the discriminative learning branch, the restorative learning branch, and the adversarial learning branch comprises:

implementing a Discriminative, Restorative, and Adversarial learning framework (DiRA framework) for applying the pre-trained model of the framework to diagnosis and detection of a new medical image which forms no part of the training data received by the framework;

wherein the pre-trained model of the framework is to render a prediction as to presence or absence of a disease within the new medical image or to segment lesion or organs within medical images; and outputting the prediction or segmentation as a predictive medical diagnosis for a medical patient.

3. The system of claim 1, wherein cropping the two patches from the plurality of medical images comprises one of:

cropping the two patches from one of the plurality of medical images received; or cropping the two patches from two different images within the plurality of medical images received.

4. The system of claim 1, further comprising:

iteratively cropping two patches from the plurality of medical images received;

iteratively inputting the two additional patches cropped from the plurality of medical images received as inputs into the discriminative learning branch and the restorative learning branch to generate discriminative latent features and new synthesized restorative images as output from them, respectively; and iteratively applying the adversarial learning via the adversarial learning branch to the new synthesized restorative images generated as output from the restorative learning branch to determine whether they are similar to the real medical images.

5. The system of claim 1, wherein augmenting each of the two patches at the discriminative learning branch comprises applying an augmentation function $T(\cdot)$ to generate the two augmented patches at the discriminative learning branch.

6. The system of claim 1, wherein applying the discriminative learning via the discriminative learning branch comprises processing the two augmented patches at the discriminative learning branch through encoder networks $f_\theta$ and $f_\epsilon$ of the discriminative learning branch configured for generating latent features $y_1 = f_{74}(T(x_1))$ and $y_2 = f_\epsilon(T(x_2))$.

7. The system of claim 1, wherein applying the discriminative learning via the discriminative learning branch further comprises projecting the latent features generated to a unit sphere via projection heads $h_\theta$ and $h_\epsilon$ of the discriminative learning branch configured for outputting projections $z_1 = h_\theta(y_1)$ and $z_2 = h_\epsilon(y_2)$.

8. The system of claim 1, wherein the two cropped patches received as input at each of the discriminative learning branch and the restorative learning branch are received as identical inputs.

9. The system of claim 1, wherein the discriminative learning branch comprises:

an augmentation function $T(\cdot)$ to generate the augmented patches via perturbation;

twin encoders $f_\theta$ and $f_\epsilon$ configured to generate the latent features by maximizing agreement between high-level embedding vectors of samples from a same class; and projectors $h_\theta$ and $h_\epsilon$ configured to project the latent features to a unit sphere and provide as output projections derived from the latent features.

10. The system of claim 1, wherein the restorative learning branch comprises:

an encoder $f_\theta$ and decoder $g_\theta$ configured for mapping the restorative augmented patches distorted by the augmentation function back to an original image via $f_\theta$, $g_\theta : (x, T) \mapsto x$;

wherein the encoder $f_\theta$ of the restorative learning branch is a shared encoder, shared with the discriminative learning branch; and wherein the encoder $f_\theta$ and decoder $g_{74}$ comprise an encoder/decoder network trained by maximizing a distance at pixel-level between (i) an original sample corresponding to one of the cropped patches prior to processing by the augmentation function and (ii) a restored image generated by the restorative learning branch.

11. The system of claim 1, wherein generating the discriminative latent features by training an encoder of the discriminative learning branch to maximize agreement between instances of a same class in a latent space via a discriminative loss function, comprises one of:

considering every single image amongst the plurality of medical images as a class using instance discrimination; or clustering images amongst the plurality of medical images based on a similarity metric using cluster discrimination.

12. The system of claim 11, wherein the two patches cropped and inputted into the discriminative learning branch comprise two distinct views of one identical image or two different samples from an identical cluster of images.

13. The system of claim 1, wherein generating the discriminative latent features from the discriminative learning branch comprises:
instantiating an $L_{dis}$ function utilizing one or more of cross-entropy discrimination learning, contrastive learning, and redundancy reduction learning; and
wherein the $L_{dis}$ function is configurable by an end-user to select different types of discrimination tasks without constraint via the discrimination learning branch.

14. The system of claim 1, wherein the restorative learning branch further generates fine-grained visual information at the restorative learning branch to supplement the latent features generated by the discriminative learning branch.

15. The system of claim 1, wherein the adversarial learning branch reinforces a common network encoder shared by the discriminative learning branch and the restorative learning branch by jointly optimizing the common network encoder using the adversarial loss function of the adversarial learning branch to distinguish the synthesized restorative image output by the restorative learning branch from real medical images.

16. The system of claim 1:
wherein the discriminative learning branch augments each of the two cropped patches via an image augmentation function T(•) which includes one or more of random horizontal flipping, color jittering, and Gaussian blurring of the two cropped patches; and
wherein each of the two cropped patches are further distorted by applying cutout and shuffling operations.

17. A computer-implemented method executed by a system having at least a processor and a memory therein, wherein the method comprises:
receiving training data having a plurality of medical images therein at a framework for self-supervised medical image analysis via the application of a discriminative learning branch, a restorative learning branch, and an adversarial learning branch of the framework;
cropping two patches from the plurality of medical images to generate two cropped patches;
inputting the two cropped patches into the discriminative learning branch and into the restorative learning branch to generate discriminative latent features and synthesized images from them, respectively;
generating discriminative latent features from the discriminative learning branch by: (i) receiving the two cropped patches, (ii) augmenting each of the two cropped patches to generate two augmented patches, (iii) generating latent features from the two augmented patches by training an encoder of the discriminative learning branch to maximize agreement between instances of same classes in latent space via a discriminative loss function;
generating a synthesized restorative image from the restorative learning branch by: (i) receiving the two cropped patches, (ii) distorting each of the two cropped patches to generate two distorted patches, (iii) training an encoder and decoder of the restorative learning branch to map the two distorted patches back to the two cropped patches by minimizing a distance, at a pixel-level, between each original one of the two cropped patches and a restored image generated by the restorative learning branch and (iv) outputting the synthesized restorative image from the trained encoder and decoder of the restorative learning branch;
applying adversarial learning via the adversarial learning branch of the framework by executing an adversarial discriminator to perform a min-max function for distinguishing the synthesized restorative image output by the restorative learning branch from the plurality of real medical images according to an adversarial loss function; and
outputting a pre-trained model of the framework based on the training of the discriminative learning branch and the training of the restorative learning branch and the training of the adversarial learning branch.

18. The computer-implemented method of claim 17, wherein the framework for self-supervised medical image analysis via the application of the discriminative learning branch, the restorative learning branch, and the adversarial learning branch comprises:
implementing a Discriminative, Restorative, and Adversarial learning framework (DiRA framework) for applying the pre-trained model of the framework to diagnosis and detection of a new medical image which forms no part of the training data received by the framework;
wherein the pre-trained model of the framework is to render a prediction as to presence or absence of a disease within the new medical image or to segment lesion or organs within the new medical images; and
outputting the prediction as a predictive medical diagnosis for a medical patient.

19. Non-transitory computer readable storage media having instructions stored thereupon that, when executed by a system having at least a processor and a memory therein, the instructions cause the processor to perform operations including:
receiving training data having a plurality of medical images therein at a framework for self-supervised medical image analysis via the application of a discriminative learning branch, a restorative learning branch, and an adversarial learning branch of the framework;
cropping two patches from the plurality of medical images to generate two cropped patches;
inputting the two cropped patches into the discriminative learning branch and into the restorative learning branch to generate discriminative latent features and synthesized images from each, respectively;
generating discriminative latent features from the discriminative learning branch by: (i) receiving the two cropped patches, (ii) augmenting each of the two cropped patches to generate two augmented patches, (iii) generating latent features from the two augmented patches by training an encoder of the discriminative learning branch to maximize agreement between instances of same classes in latent space via a discriminative loss function;
generating a synthesized restorative image from the restorative learning branch by: (i) receiving the two cropped patches, (ii) distorting each of the two cropped patches to generate two distorted patches, (iii) training an encoder and decoder of the restorative learning branch to map the two distorted patches back to the two cropped patches by minimizing a distance, at a pixel-level, between each original one of the two cropped patches and a restored image generated by the restorative learning branch and (iv) outputting the synthesized restorative image from the trained encoder and decoder of the restorative learning branch;

applying adversarial learning via the adversarial learning branch of the framework by executing an adversarial discriminator to perform a min-max function for distinguishing the synthesized restorative image output by the restorative learning branch from the plurality of real medical images according to an adversarial loss function; and outputting a pre-trained model of the framework based on the training of the discriminative learning branch and the training of the restorative learning branch and the training of the adversarial learning branch.

20. The non-transitory computer readable storage media of claim 19, wherein the framework for self-supervised medical image analysis via the application of the discriminative learning branch, the restorative learning branch, and the adversarial learning branch comprises:

implementing a Discriminative, Restorative, and Adversarial learning framework (DiRA framework) for applying the pre-trained model of the framework to diagnosis and detection of a new medical image which forms no part of the training data received by the framework;

wherein the pre-trained model of the framework is to render a prediction as to presence or absence of a disease within the new medical image or to segment lesion or organs within new medical images; and outputting the prediction as a predictive medical diagnosis for a medical patient.

* * * * *